US011806372B2

(12) United States Patent
Hall et al.

(10) Patent No.: US 11,806,372 B2
(45) Date of Patent: Nov. 7, 2023

(54) METHODS OF TREATING AND DIAGNOSING IBD ASSOCIATED WITH R. GNAVUS AND/OR R. GNAVUS GROUP IBD COLONIZATION

(71) Applicants: The Broad Institute, Inc., Cambridge, MA (US); The General Hospital Corporation, Boston, MA (US); President and Fellows of Harvard College, Cambridge, MA (US)

(72) Inventors: Andrew Brantley Hall, Cambridge, MA (US); Ramnik Xavier, Brookline, MA (US); Curtis Huttenhower, Boston, MA (US); Moran Yassour, Cambridge, MA (US); Hera Vlamakis, Arlington, MA (US)

(73) Assignees: The Broad Institute, Inc., Cambridge, MA (US); The General Hospital Corporation, Boston, MA (US); President and Fellows of Harvard College, Cambridge, MA (US)

( * ) Notice: Subject to any disclaimer, the term of this patent is extended or adjusted under 35 U.S.C. 154(b) by 279 days.

(21) Appl. No.: 16/604,866

(22) PCT Filed: Apr. 20, 2018

(86) PCT No.: PCT/US2018/028604
§ 371 (c)(1),
(2) Date: Oct. 11, 2019

(87) PCT Pub. No.: WO2018/195448
PCT Pub. Date: Oct. 25, 2018

(65) Prior Publication Data
US 2020/0155617 A1   May 21, 2020

Related U.S. Application Data

(60) Provisional application No. 62/488,554, filed on Apr. 21, 2017.

(51) Int. Cl.
*A61K 35/741* (2015.01)
*A61P 29/00* (2006.01)

(52) U.S. Cl.
CPC .......... *A61K 35/741* (2013.01); *A61P 29/00* (2018.01)

(58) Field of Classification Search
CPC ........ A61K 39/00; A61K 48/00; A61K 49/00; A01N 63/00
USPC ............... 424/9.1, 9.2, 93.1, 93.2, 93.4
See application file for complete search history.

(56) References Cited

U.S. PATENT DOCUMENTS 10,300,173 B2 * 5/2019 Burgess ............... A61P 17/02
10,668,116 B2 * 6/2020 Cutcliffe ............. A61K 35/745
2013/0045874 A1 * 2/2013 Ehrlich ................ C12Q 1/6883
435/6.12

OTHER PUBLICATIONS

Cervera-Tison et al., (2012) Applied and Environmental Microbiology, 78(21):7720-7732.*
Hansen et al. (Journal of Clinical Microbiology, 51(4):1334-1336, Apr. 2013.*
Hansen et al. Journal of Clinical Microbiology, vol. 51, No. 4. pp. 1334-1336, Apr. 2013 (Year: 2013).*
Abubucker et al. "Metabolic Reconstruction for Metagenomic Data and Its Application to the Human Microbiome" PLOS Computational Biology, 8(6): e1002358 (2012).
Albenberg et al. "Correlation Between Intraluminal Oxygen Gradient and Radial Partitioning of Intestinal Microbiota in Humans and Mice" *Gastroenterology*, 147(5): 1055-1063 (2014).
Ballal et al. "Host lysozyme-mediated lysis of Lactococcus lactis facilitates delivery of colitis-attenuating superoxide dismutase to inflamed colons" *Proceedings of the National Academy of Sciences*, 112(25): 7803-7808 (2015).
Balmus et al. "The Implications of Oxidative Stress and Antioxident Therapies in Inflammatory Bowel Disease: Clinical Aspects and Animal Models." 22(1): 3-17 (2016).
Coskun "Intestinal epithelium in inflammatory bowel disease" frontiers in Medicine, vol. 1, Article 2: 1-5 (2014).
Crost et al. "Utilization of Mucin Glycans by the Human Gut Symbiont *Ruminococcus gnavus* Is Strain-Dependent," *PLOS ONE*, 8(10): e76341 (2013).
Crost et al. "The mucin-degradation strategy of Ruminococcus gnavus: The importance of intramolecular trans-sialidases" *Gut Microbes*, 7(4): 302-312 (2016).
El Mazouari et al. "F17-Like Fimbriae from an Invasive *Escherichia coli* Strain Producing Cytotoxic Necrotizing Factor Type 2 Toxin" *Infection an Imunity*, 62(6): 2633-2638 (1994).
Franzosa et al. "Identifying personal microbiomes using metagenomic codes," *Proceeding of the National Academy of Sciences*, E2930-E2938 (2015).
Hall et al. "A novel Ruminococcus gnavus clade enriched in inflammatory bowel disease patients," Genome Medicine 9(1):103 (2017).
Hansen et al. "Two Cases of *Ruminococcus gnavus* Bacteremia Associated with Diverticulitis," *Journal of Clinical Microbiology*, 51(4): 1334-1336 (2013).
The Human Microbiome Project Consortium "Structure, Function and Diversity of the Healthy Human Microbiome," *Nature*, 486(7402): 207-214 (2012).
Imam et al. "Identification of Surprisingly Diverse Type IV Pili, across a Broad Range of Gram-Positive Bacteria," *PLOS One*, 6(12): e28919 (2011).
International Search Report and Written Opinion dated Jul. 26, 2018 in PCT Application No. PCT/US2018/028604, 16 pages.

(Continued)

*Primary Examiner* — Jana A Hines
*Assistant Examiner* — Khatol S Shahnan Shah
(74) *Attorney, Agent, or Firm* — McNeill Baur PLLC

(57) ABSTRACT

This application provides for methods of treatment for IBD, especially in subjects who have *R. gnavus* species or *R. gnavus* group IBD strains as a component of their microbiome. The application also provides for methods of diagnosing IBD, as well as kits for use in the claimed methods.

21 Claims, 18 Drawing Sheets

(56) References Cited

OTHER PUBLICATIONS

Joossens et al. "Dysbiosis of the faecal microbiota in patients with Crohn's disease and their unaffected relatives," *Gut,* 60: 631-637 (2011).
Juste et al. "Bacterial protein signals are associated with Crohn's disease," *Gut,* 63: 1566-1577 (2014).
Kish et al. "Effects of Probiotics on Host Immune Function and Behavior Are Dependent Upon Genotype and Diet," *Gastroenterology,* 140(5): S-19 (2011).
Knights et al. "Complex host genetics influence the microbiome in inflammatory bowel disease," *Genome Medicine,* 6: 107 (2014).
Kostic et al. "The Dynamics of the Human Infant Gut Microbiome in Development and in Progression towards Type 1 Diabetes," *Cell Host Microbe,* 17(2): 260-273 (2015).
Lawson and Finegold "Reclassification of Ruminococcus obeum as Blautia obeum comb. nov." *Internal Journal of Systemic and Evolutionary Microbiology,* 65:789-793 (2015).
Lewis et al. "Inflammation, Antibiotics, and Diet as Environmental Stressors of the Gut Microbiome in Pediatric Crohn's Disease," *Cell Host Microbe,* 18(4): 489-500 (2015).
Liu et al. "Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., Blautia hansenii comb. nov., Blautia hydrogenotrophica comb. nov., Blautia luti comb. nov., Blautia producta comb. nov., Blautia schinkii comb. nov. and description of *Blautia wexlerae* sp. nov., isolated from human faeces," *Internal Journal of Systemic and Evolutionary Microbiology,* 58: 1896-1902 (2008).
Liu et al. "Glycine betaine improves oxidative stress tolerance and biocontrol efficacy of the antagonistic yeast *Cystofilobasidium infirmominiatum*" *International Journal of Food Microbiology,* 146(1): 76-83 (2011).
Martinez-Medina and Garcia-Gil "*Escherichia coli* in chronic inflammatory bowel diseases: An update on adherent invasive *Escherichia coli* pathogenicity," 5(3): 213-227 (2014).
Michielan and D'Incà "Intestinal Permeability in Inflammatory Bowel Disease: Pathogenesis, Clinical Evaluation, and Therapy of Leaky Gut" *Mediators of Inflammation,* vol. 2015, Article ID 628157, 10 pages (2015).
Monk et al. "Diets enriched with cranberry beans alter the microbiota and mitigate colitis severity and associated inflammation," The Journal of Nutritional Biochemistry 28(1): 129-139 (2016).
Moore et al. "Emendation of Bacteroidaceae and Butyrivibrio amd Descriptions of *Desulfomonas* gen. nov. and Ten New Species in the Genera *Desulfomonas, Butyrivibriom Eubacterium. Clostridium,* and *Ruminococcus,*" *International Journal of Systematic Bacteriology,* 26(2): 238-252 (1976).
Morgan et al. "Dysfunction of the intestinal microbiome in inflammatory bowel disease and treatment," *Genome Biology,* 13: R79, 18 pages (2012).
Pierce et al. "The Complete Genome Sequence of *Moorella thermoacetica* (f. *Clostridium thermoaceticum*)," *Environ Microbiology,* 10(10): 2550-2573 (2008).
Png et al. "Mucolytic Bacteria With Increased Prevalence in IBD Mucosa Augment In Vitro Utilization of Mucin by Other Bacteria," *American Journal of Gastroenterology,* 105(1): 2420-2428 (2010).
Poulsen et al. "Comparative analysis of inflamed and non-inflamed colon biopsies reveals strong proteomic inflammation profile in patients with ulcerative colitis," *BMC Gastroenterology,* 12:76, 11 pages (2012).
Reunanen et al. "*Akkermansia muciniphila* Adheres to Enterocytes and Strengthens the Integrity of the Epithelial Cell Layer," *Applied and Environmental Microbiology,* 81(11): 3655-3662 (2015).
Rey et al. "Dissecting the in Vivo Metabolic Potential of Two Human Gut Acetogens," *The Journal of Biological Chemistry,* 285(29): 22082-22090 (2010).
Sabet et al. "LPXTG Protein InlJ, a Newly Identified Internalin Involved in *Listeria monocytogenes* Virulence," *Infection and Immunity,* 73(10): 6912-6922 (2005).
Seril et al. "Oxidative stress and ulcerative colitis-associated carcinogenesis: studies in humans and animal models," *Carcinogenesis,* 24(3): 353-362 (2003).
Shaw et al. "Dysbiosis, inflammation, and response to treatment: a longitudinal study of pediatric subjects with newly diagnosed inflammatory bowel disease," *Genome Medicine,* 8:75, 13 pages (2016).
Simms et al. "Reduced α-defensin expression is associated with inflammation and not NOD2 mutation status in ileal Crohn's disease" *Gut,* 57(7): 903-910 (2008).
Strugala et al. "Thickness and continuity of the adherent colonic mucus barrier in active and quiescent ulcerative colitis and Crohn's disease," *International Journal of Clinical Practice,* 62: 762-769 (2008).
Sun et al. "Epithelial Sel1L is required for the maintenance of intestinal homeostasis," *Molecular Biology of the Cell,* 27: 483-490 (2016).
Suvorova et al. "GntR Family of Bacterial Transcription Factors and Their DNA Binding Motifs: Structure, Positioning and Co-Evolution," *POLS One,* 10(7): e0132618 (2015).
Tailford et al. "Discovery of intramolecular trans-sialidases in human gut microbiota suggests novel mechanisms of mucosal adaptation," *Nature Communications,* 6: 7624, pp. 1-12 (2015).
Truong et al. "MetaPhlAn2 for enhanced metagenomic taxonomic profiling," *Nature Methods,* 12: 902-903 (2015) (PMID 26418763).
Vaarala et al. "The "Perfect Storm" for Type 1 Diabetes: The Complex Interplay Between Intestinal Microbiota, Gut Permeability, and Mucosal Immunity" *Diabetes* 57(10): 2555-2562 (2008).
Von Schillde et al. "Lactocepin Secreted by Lactobacillus Exerts Anti-Inflammatory Effects By Selectively Degrading Proinflammatory Chemokines," *Cell Host & Microbe,* 11: 387-396 (2012).
Whittaker and Hynes "Distribution and Evolution of von Willebrand/Integrin A Domains: Widely Dispersed Domains with Roles in Cell Adhesion and Elsewhere," *Molecular Biology of the Cell,* 13: 3369-3387 (2002).
Yassour et al. "Natural history of the infant gut microbiome and impact of antibiotic treatment on bacterial strain diversity and stability," *Science Trans. Med.* 8(343): 343ra81 (2016).

\* cited by examiner

METHODS OF TREATING AND DIAGNOSING IBD ASSOCIATED WITH R. GNAVUS AND/OR R. GNAVUS GROUP IBD COLONIZATION

FIELD

Methods of Treatment and Diagnostic Methods for IBD.

BACKGROUND

Inflammatory bowel disease (IBD) is a chronic inflammatory disease of gastrointestinal tract with two main clinical manifestations: Crohn's disease and ulcerative colitis. The pathogenesis of IBD in genetically susceptible individuals likely involves an overactive immune response to the gut microbiome. Coskun, Intestinal Epithelium in Inflammatory Bowel Disease, Frontiers in Medicine 1, Article 22:1-5, doi:10.3389/fmed.2014.00024 (2014). Changes in the intestinal microenvironment may contribute to the altered gut microbial community composition in IBD. The inflammation of IBD is associated with increased generation of reactive oxygen species (ROS) and reactive nitrogen species (RNS) causing oxidative stress for both the host and gut microbiome. Balmus et al., The Implications of Oxidative Stress and Antioxidant Therapies in Inflammatory Bowel Disease: Clinical Aspects and Animal Models, The Saudi Journal of Gastroenterology 22(1):3-17, doi:10.4103/1319-3767.173753 (2016). Previous studies on the gut microbiome in IBD have noted the increased abundance of pathways involved in the microbial response to oxidative stress and increases in species which can tolerate oxidative stress. Id. However, these studies have not explicitly addressed how the shift in the gut microbiome in IBD is related to the ability of microbes to deal with the increased oxidative stress.

In IBD, inflammation of the gastrointestinal tract results in increased production of ROS and RNS. Seril et al., Oxidative Stress and Ulcerative Colitis-associated Carcinogenesis: Studies in Humans and Animals Models, Carcinogenesis 24(3):353-362 (2003). Increased levels of ROS and RNS have been implicated in the pathogenesis of IBD, and oxidative stress response proteins have increased abundance in IBD. Poulsen et al., Comparative Analysis of Inflamed and Non-inflamed Colon Biopsies Reveals Strong Proteomic Inflammation Profile in Patients with Ulcerative Colitis, BMC Gastroenterology 12(76):1-11 (2012); Seril et al., Oxidative Stress and Ulcerative Colitis-associated Carcinogenesis: Studies in Humans and Animals Models, Carcinogenesis 24(3):353-362 (2003). Mitigating oxidative stress caused by ROS and RNS may provide an avenue to treat IBD. Superoxide dismutase, an enzyme that detoxifies superoxide, from the *Lactococcus* was responsible for the beneficial effect of this organism. Ballal et al., Host Lysozyme-mediated Lysis of *Lactococcus lactis* Facilitates Delivery of Colitis-attenuating Superoxide Dismutase to Inflamed Colons, Proc Natl Acad Sci USA 112(25):7803-7808 (2015).

The increased oxidative stress of the IBD gut is implicated in some of the changes in the composition of the gut microbiome in IBD. Juste et al., Bacterial Protein Signals are Associated with Crohn's Disease, Gut 63:1566-1577, doi: 10.1136/gutjnl-2012-303786 (2014). Different species from the gut microbiome have different susceptibilities to oxidative stress. For example, facultative anaerobes, such as *Escherichia coli*, use oxygen when it is present, and therefore possess mechanisms, such as expression of superoxide dismutase and catalase, to respond to oxidative stress. Aerotolerant anaerobes, such as the *Bacteroides* species, possess the enzymes necessary to respond to oxidative stress and can survive atmospheric levels of oxygen for extended periods but do not perform oxidative respiration. Obligate anaerobes, such as *Roseburia* species, lack adequate responses to oxidative stress, and therefore die when exposed to reactive oxygen species. Previous studies have also consistently shown that the Enterobactericeae, and specifically the facultative anaerobe *E. coli*, has increased abundance in IBD. Knights et al., Complex Host Genetics Influence the Microbiome in Inflammatory Bowel Disease, Genome Medicine 6:107 (2014). Further studies have noted a decrease of obligate anaerobes in IBD. Lewis et al., Inflammation, Antibiotics, and Diet as Environmental Stressors of the Gut Microbiome in Pediatric Crohn's Disease, Cell Host Microbe 18(4):486-500, doi:10.1016/j.chom.2015.09.008 (2015). Pathways involved in cysteine and glutathione metabolism, as well as sulfate transport, which are involved in the production of products that protect against oxidative stress, show increased abundance in IBD. Morgan et al., Dysfunction of the Intestinal Microbiome in Inflammatory Bowel Disease and Treatment, Genome Biology 13:R79 (2012). Thus, oxidative stress appears to be a major factor shaping the dysbiosis of the gut microbiome in IBD.

*R. gnavus* is a member of the phylum Firmicutes present in the gut of ~90% individuals, though at low abundance. The Human Microbiome Project Consortium, Structure, Function and Diversity of the Healthy Human Microbiome, Nature 486(7402):207-214 (2012). Originally classified in the genus *Ruminococcus* by Moore et al. (Emendation of Bacteroidaceae and *Butyrivibrio* and Descriptions of *Desulfomonas* gen. nov. and Ten New Species in the General *Desulfomonas, Butyrivibio, Eucabterium, Clostridium*, and *Ruminococcus*, International Journal of Systematic Bacteriology 26(2):238-252, doi: 10.1099/00207713-26-2-238 (1976)), *R. gnavus* has been recently transferred to the genus *Blautia* based on 16s rRNA sequencing. Liu et al., Reclassification of *Clostridium coccoides, Ruminococcus hansenii, Ruminococcus hydrogenotrophicus, Ruminococcus luti, Ruminococcus productus* and *Ruminococcus schinkii* as *Blautia coccoides* gen. nov., comb. nov., *Blautia hansenii* comb. nov., *Blautia luki* comb. nov., *Blautia producta* comb. nov., *Blautia schinkii* comb. nov. and description of *Blautia weskrae* sp. nov. Isolated from Human Faeces, International Journal of Systematic and Evolutionary Microbiology 58:1896-1902 (2008); Lawson and Finegold, Reclassification of *Ruminococcus obeum* as *Blautia obeum* comb. nov., International Journal of Systematic and Evolutionary Microbiology 65:789-793 (2015). The original misclassification of *R. gnavus* combined with the limitations of 16s sequencing for accurate species-level identification has confounded analysis of the abundance of *R. gnavus* in previous IBD studies, and left the significance of *R. gnavus* in the dysbiosis of IBD unappreciated. The increased abundance of *R. gnavus* in IBD compared to healthy individuals has only been noted in a few previous studies using primers specific for the *R. gnavus* 16s rRNA and denaturing gradient gel electrophoresis (DGGE). Png et al., Mucolytic Bacteria with Increased Prevalence in IBD Mucosa Augment In Vitro Utilization of Mucin by Other Bacteria, American Journal of Gastroentrolgy 105(1):2420-2428 (2010); Joossens et al., Dysbiosis of the Faecal Microbiota in Patients with Crohn's Disease and Their Unaffected Relatives, Gut 60:631-637 (2011); Morgan et al., Dysfunction of the Intestinal Microbiome in Inflammatory Bowel Disease and Treatment, Genome Biology 13:R79 (2012). In addition to its increased abundance in IBD, other studies have implicated *R. gnavus* as a potential pathobiont as it was responsible for bacteremia in patients with diverticulitis (Hansen et al., Two Cases of *Ruminococcus gnavus* Bacterimia Associated with Diverticulitis, Journal of Clinical Microbiology 51(4):1664-1336 (2013)) and displayed increased abundance in stool from type 1 diabetes patients (Kostic et al., The Dynamics of the Human Infant Gut Microbiome in Development and In Progression Towards Type 1 Diabetes, Cell Host Microbe 17(2):260-276 (2015)). The accurate species-level identification afforded by whole metagenome sequencing is critical to survey the abundance of *R. gnavus*.

SUMMARY

In accordance with the description, a method of treating IBD in a human subject comprises administering an effective amount of at least one antimicrobial agent effective for eliminating or suppressing *R. gnavus*.

A method of treating IBD in a human subject comprises administering an effective amount of at least one IBD therapy to a subject having a gut microbiome comprising *R. gnavus*.

A method of diagnosing IBD in a human subject comprises: (a) determining from a gut microbiome sample whether the gut microbiome comprises *R. gnavus* and (b) diagnosing the subject as having IBD when *R. gnavus* is identified.

In some embodiments, wherein the IBD is Crohn's disease or ulcerative colitis.

In some embodiments, the IBD is collagenous colitis, lymphocytic colitis, diversion colitis, Behcet's disease, or indeterminate colitis.

In some embodiments, *R. gnavus* has at least 5% relative abundance in the subject.

In some embodiments, *R. gnavus* has at least 10%, 20%, 30%, or 40% relative abundance in the subject.

In some embodiments, the strain of *R. gnavus* is *R. gnavus* group IBD.

In some embodiments, the *R. gnavus* comprises adherence-related genes.

In some embodiments, the *R. gnavus* comprises genes involved in glycine-betaine transport.

In some embodiments, the *R. gnavus* comprises at least one gene from Table 7.

In some embodiments, the *R. gnavus* comprises at least one cluster 1 gene from Table 7.

In some embodiments, the *R. gnavus* comprises at least one cluster 2 gene from Table 7.

In some embodiments, the *R. gnavus* comprises at least one cluster 3 gene from Table 7.

In some embodiments, the *R. gnavus* comprises at least one cluster 4 gene from Table 7.

In some embodiments, the *R. gnavus* comprises all the genes from Table 7.

In some embodiments, the *R. gnavus* is missing the Acetyl-CoA synthetase gene.

In some embodiments, the *R. gnavus* is missing the corrinoid iron-sulfur small subunit.

In some embodiments, the *R. gnavus* comprises genes for mucus utilization.

In some embodiments, the *R. gnavus* comprises at least one glycoside hydrolase gene.

In some embodiments, the *R. gnavus* comprises at least one of the glycoside hydrolase genes identified in Table 9.

In some embodiments, the *R. gnavus* comprises at least one of the glycoside hydrolase genes chosen from: g000676, g001578, g001597, g002881, g002982, g003046, g003139, g003144, g003577, g003631, g004607, g005357, g006085, g006118, and g007627.

In some embodiments, the *R. gnavus* comprises at least 2, 3, 4, 5, 6, 7, 8, 9, 10, 11, 12, 13, 14, or 15 of the glycoside hydrolase genes chosen from: g000676, g001578, g001597, g002881, g002982, g003046, g003139, g003144, g003577, g003631, g004607, g005357, g006085, g006118, and g007627.

In some embodiments, multiple samples of the subject's gut microbiome are obtained over time.

In some embodiments, the relative abundance of *R. gnavus* varies over time.

In some embodiments, the relative abundance differs between samples by at least 5%, 10%, 15%, 20%, 25%, or 30%.

In some embodiments, the gut microbiome sample is obtained from stool.

In some embodiments, the gut microbiome sample is obtained from a biopsy of the mucus lining of the gastrointestinal tract.

In some embodiments, the mucus lining of the gastrointestinal tract is the mucus lining of the small intestine.

In some embodiments, the mucus lining of the gastrointestinal tract is the mucus lining of the large intestine.

In some embodiments, the IBD therapy comprises: (a) at least one pharmaceutical composition; (b) at least one phage therapy; (c) at least one probiotic agent; (d) at least one lifestyle modification; (e) at least one alternative medicine; and/or (f) surgery.

In some embodiments, the IBD therapy comprises at least one pharmaceutical composition.

In some embodiments, the IBD therapy comprises at least one phage therapy.

In some embodiments, the IBD therapy comprises at least one probiotic agent.

In some embodiments, the IBD therapy comprises at least one lifestyle modification.

In some embodiments, the IBD therapy comprises at least one alternative medicine.

In some embodiments, the IBD therapy comprises at least one surgery.

In some embodiments, at least one pharmaceutical composition is chosen from at least one antimicrobial agent, aminosalicylate, corticosteroid, immune system suppressor, anti-diarrheal agent, and pain reliever.

In some embodiments, the antimicrobial agent is chosen from benzylpenicillin, piperacillin-tazobactam, meropenem, clindamycin, metronidazole, moxifloacin, vancomycin, tigecycline, bacitracin, and ciprofloxacin.

In some embodiments, the aminosalicylates are chosen from 5-aminosalicylates, sulfasalazine, mesalamine, balsalazide, and olsalazine.

In some embodiments, the at least one corticosteroid is chosen from prednisone and hydrocortisone.

In some embodiments, the at least one immune system suppressor is chosen from at least one azathioprine, mercaptopurine, cyclosporine, TNF-alpha inhibitors, methotrexate, integrin inhibitors, and ustekinumab.

In some embodiments, the at least one TNF-alpha inhibitor is chosen from an anti-TNF-alpha antibody or antigen binding fragment thereof.

In some embodiments, the anti-TNF-alpha antibody or antigen binding fragment thereof is chosen from infliximab, adalimumab, golimumab, and antigen binding fragments thereof.

In some embodiments, the at least one integrin inhibitor is chosen from an anti-integrin antibody or antigen binding fragment thereof.

In some embodiments, the anti-integrin antibody or antigen binding fragment thereof is chosen from natalizumab, vedolizumab, and antigen binding fragments thereof.

In some embodiments, the anti-diarrheal agent is chosen from a fiber supplement (such as *psyllium* powder or methylcellulose) or loperamide.

In some embodiments, the pain reliever is acetaminophen.

In some embodiments, the pain reliever is not ibuprofen, naproxen sodium, or diclofenac sodium.

In some embodiments, the at least one probiotic agent comprises one or more normal inhabitants of the human intestinal tract.

In some embodiments, the at least one probiotic agent is chosen from *Bacteroides, Prevotella, Porphyromonas, Fusobacterium, Sutterella, Bilophila, Campylobacter, Wolinella, Butyrovibrio, Megamonas, Desulfomonas, Desulfovibrio, Bifidobacterium, Lactobacillus, Eubacterium, Actinomyces, Eggerthella, Coriobacterium, Propionibacterium, Bacillus, Peptostreptococcus, Peptococcus, Acidaminococcus, Ruminococcus, Megasphaera, Gaffkya, Coprocaccus, Veillonella, Sarcina, Clostridium, Aerococcus, Streptococcus, Enterococcus, Pediococcus, Micrococcus, Staphylococcus, Corynebacterium*, Enterobacteriaceae, Pseudomonadaceae, and mixtures thereof.

In some embodiments, at least one lifestyle modification is chosen from stopping smoking, stopping isotretinoin use, stopping nonsteroidal anti-inflammatory medication use, and dietary modification, and at least one alternative medicine.

In some embodiments, dietary modification is chosen from iron supplements, B-12 supplements or shots, calcium supplements, vitamin D supplements, enteral nutrition, parenteral nutrition, a low-residue and/or low fiber diet, reducing dairy products, reducing lactose consumption, a low-fat diet, avoiding uncooked fruits and vegetables, reducing irritating foods (including reducing foods in the cabbage family (broccoli, cauliflower, cabbage), reducing nuts and seed, reducing corn and popcorn, reducing spicy foods, reducing alcohol, and reducing caffeine), eating smaller and more frequent meals, drinking more liquids, and taking a multivitamin.

In some embodiments, at least one lifestyle modification is chosen from exercise, biofeedback, and regular relaxation and breathing exercises.

In some embodiments, the at least one alternative medicine comprises fish oil supplement, aloe vera supplement, turmeric or curcumin supplement, and acupuncture.

In some embodiments, the surgery is chosen from removing a bowel obstruction, repairing or removing ulcers, draining and/or repairing abscesses, repairing or removing fistulas, removing inflamed and/or narrowed portions of the gastrointestinal tract, proctocolectomy, and strictureplasty.

In some embodiments, the phage therapy is lytic phage specific for *R. gnavus*.

In some embodiments, the lytic phage is obtained from stool samples.

In some embodiments, further diagnostic information is obtained from a procedure chosen from at least one of colonoscopy, flexible sigmoidoscopy, upper endoscopy, capsule endoscopy, double-balloon endoscopy, x-ray, CT scan, MRI, and small bowel imaging.

A kit to detect *R. gnavus* from a gut microbiome sample comprises (a) an agent for detecting *R. gnavus* and/or *R. gnavus* group IBD; and (b) optionally buffers and/or reaction solutions.

In some embodiments, the kit can detect *R. gnavus* group IBD.

In some embodiments, the agent for detecting *R. gnavus* and/or *R. gnavus* group IBD is chosen from: (a) at least one nucleic acid probe capable of hybridizing to a *R. gnavus* nucleic acid; (b) at least one primer pair for amplifying a *R. gnavus* nucleic acid; and (c) an antibody or antigen binding fragment thereof specific for *R. gnavus*.

In some embodiments, the *R. gnavus* nucleic acid is at least one of the genes in Table 7 or Table 9. In some embodiments, the *R. gnavus* nucleic acid is a 16S rRNA gene.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 2B-H shows a selection of individuals as illustrative examples.

FIGS. 3B and C show relative abundance of *R. gnavus* in IBD patients after diagnosis, with the time post diagnosis plotted on the X-axis.

FIG. 7A shows a phylogenetic tree of *R. gnavus* strains in DIABIMMUNE samples, with existing isolate genomes associated with circles and samples from T1D-positive infants depicted with squares and triangles; Xavier lab isolates were described in Hall et al., Genome Med 9(1):103 (published online Nov. 28, 2017). FIG. 7B shows the presence of selected CRISPR-related and other genes with differential prevalences between the clades.

DESCRIPTION OF THE EMBODIMENTS

Figure 1A:
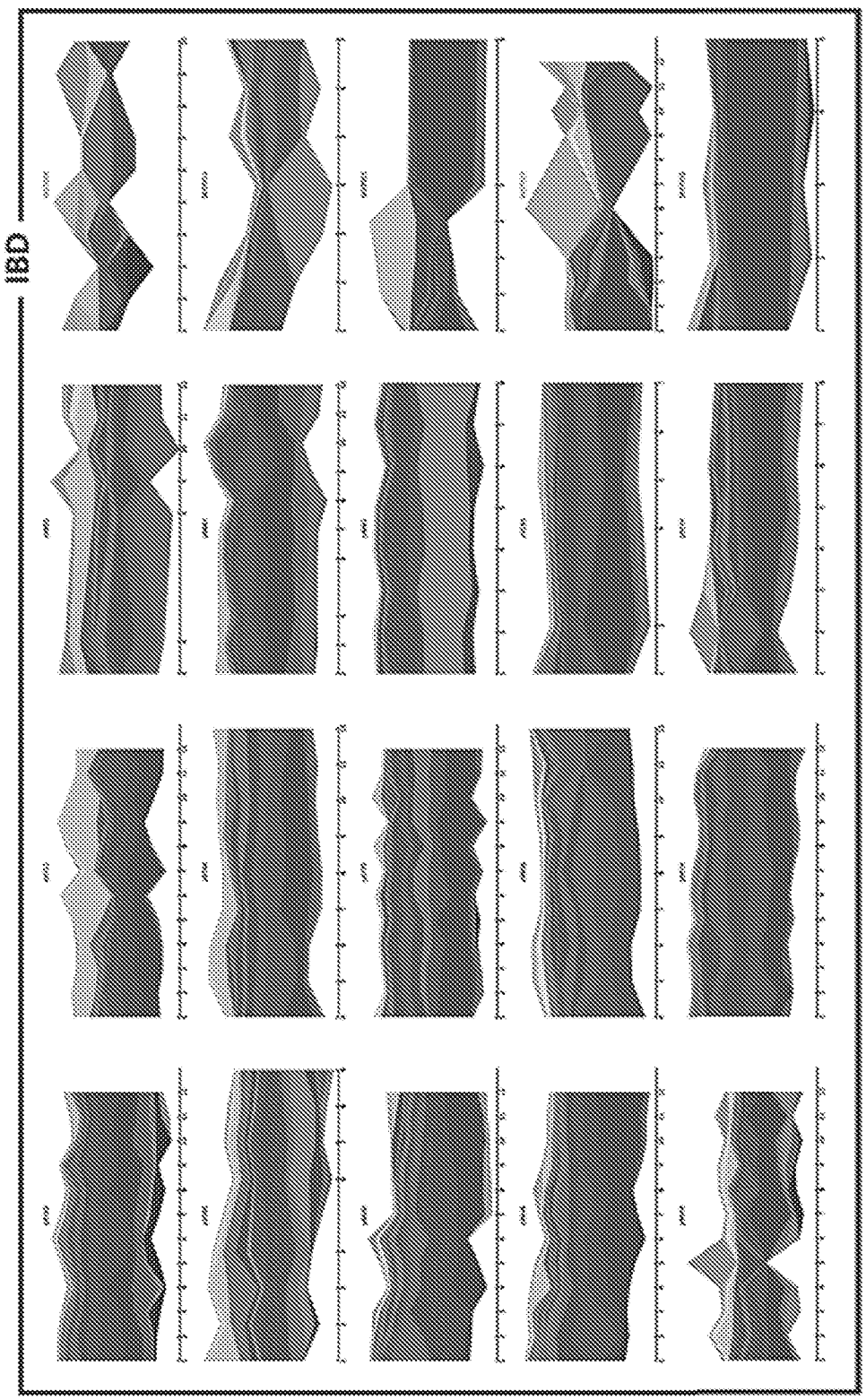
FIGS. 1A-B provide an overview of genus abundance over time for individual IBD (FIG. 1A) or control subjects (FIG. 1B), performed according to the method set forth in Yassour et al. Science Trans. Med. 8(343): 343ra81 (2016). Each plot represents the microbial trajectory of a single individual, with different tones of shading indicating bacteria of different phyla. See also Hall et al, Genome Med 9(1):103 (published online Nov. 28, 2017).

Inflammatory bowel disease (IBD) is characterized by chronic inflammation of the gastrointestinal tract that has been linked to deviations in the composition of the gut microbiome. Using taxonomic profiling and reference genomes, we inferred an increased abundance of oxidative stress pathways in IBD. To better understand the mechanisms underlying the changes between gut metagenomes of individuals with IBD relative to non-IBD controls, we performed whole metagenome sequencing (WMS) on monthly stool samples from 32 subjects (n=20 IBD; 12 control), resulting in 266 total longitudinal samples. Combining taxonomic and functional profiling, increased disease activity was characterized by a loss of strict anaerobes coupled with an increased abundance of facultative anaerobes that are typically found only in very low abundance in healthy individuals. Facultative anaerobes were significantly enriched in stool samples from individuals with IBD (nested anova+p-value=0.0478, validation cohort nested anova+p-value=0.005) adding further evidence to the hypothesis that increased oxidative stress may be a major factor shaping the microbial dysbiosis observed in IBD. We also found dramatic, but transient increases in the relative abundance of *Ruminococcus gnavus* in IBD. Strain-level analysis supports the existence of an IBD-specific strain of *R. gnavus* with a distinct functional repertoire compared *R. gnavus* from healthy individuals. The IBD-specific strain contains adherence-related genes and genes involved in glycine-betaine transport which are involved in the response to stress. Pangenome analysis of *R. gnavus* revealed that genes for mucus utilization are widespread in our samples suggesting this organism occupies the mucogenic niche and is therefore closely-associated with the host epithelia. Increases in the abundance of mucus-utilizing, epithelial-associated strains of *R. gnavus* are a part of the dysbiotic consortia that may contribute to the excessive response of the host immune system to the gut microbiome in IBD.

I. Methods of Treatment

In some embodiments, a method of treating IBD in a human subject comprises administering an effective amount of at least one antimicrobial agent effective for eliminating or suppressing *R. gnavus*.

In some embodiments, a method of treating IBD in a human subject comprises administering an effective amount of at least one IBD therapy to a subject having a gut microbiome comprising *R. gnavus*.

A. IBD Therapies

In some embodiments, methods of treatment for IBD, or IBD therapies, may comprise at least one of: (a) at least one pharmaceutical composition; (b) at least one phage therapy; (c) at least one probiotic agent; (d) at least one lifestyle modification; (e) at least one alternative medicine; and/or (f) at least one surgery.

1. Pharmaceutical Compositions

In some embodiments, at least one pharmaceutical composition is chosen from at least one antimicrobial agent, aminosalicylate, corticosteroid, immune system suppressor, anti-diarrheal agent, and pain reliever.

a) Antimicrobials Against *R. gnavus*

Antimicrobial therapy can be started to inhibit or eliminate the *R. gnavus* associated with IBD. The antimicrobials used may have certain characteristics for optimal benefit and minimal side effects. In some embodiments, an antimicrobial selected as a therapy may have one or more of the following properties:

1. Good in vitro activity against most or all *R. gnavus* species or most or all *R. gnavus* group IBD strains;
2. Relatively poor activity against most other organisms normally found in the gut flora;
3. Safe doses capable of achieving a concentration in the colon exceeding the minimal inhibitory concentration or minimal bactericidal concentration of the drug by at least four or five two-fold concentrations;
4. Preferably absorbed very little or not at all when given orally (to minimize systemic effects);
5. Bactericidal activity preferred (rather than purely inhibitory activity);
6. Not cross-resistant with vancomycin or other drugs that are important for treatment of systemic infections;
7. Resistance doesn't develop readily: (i.e., the drug does not readily engender resistance in bacteria);
8. Well tolerated orally over an extended period of time (preferably at least 3-4 months);
9. Little or no toxicity, either systemically or in the bowel;
10. Effective when given only once or twice daily; and
11. Moderate in price.

In some embodiments, the antimicrobial agent is chosen from benzylpenicillin, piperacillin-tazobactam, meropenem, clindamycin, metronidazole, moxifloacin, vancomycin, tigecycline, bacitracin, and ciprofloxacin. Aminosalicylates include, but are not limited to, 5-aminosalicylates, sulfasalazine, mesalamine, balsalazide, and olsalazine. Corticosteroids include, but are not limited to, prednisone and hydrocortisone.

At least one immune system suppressor includes, but is not limited to, at least one azathioprine, mercaptopurine, cyclosporine, TNF-alpha inhibitors, methotrexate, integrin inhibitors, and ustekinumab. At least one TNF-alpha inhibitor may be chosen from an anti-TNF-alpha antibody or antigen binding fragment thereof. In some instances, the anti-TNF-alpha antibody or antigen binding fragment thereof is chosen from infliximab, adalimumab, golimumab, and antigen binding fragments thereof. In some methods, the at least one integrin inhibitor is chosen from an anti-integrin antibody or antigen binding fragment thereof. The anti-integrin antibody or antigen binding fragment thereof may be chosen from natalizumab, vedolizumab, and antigen binding fragments thereof.

In some embodiments, the anti-diarrheal agent is chosen from a fiber supplement (such as *psyllium* powder or methylcellulose) or loperamide.

In some embodiments, the pain reliever is acetaminophen. In some embodiments, the pain reliever is not ibuprofen, naproxen sodium, or diclofenac sodium.

2. Phage Therapy

Phage (otherwise known as bacteriophage) therapy can also be used to treat IBD. Specifically, phage specific for *R. gnavus* can be used to inhibit or eliminate the *R. gnavus* associated with IBD. Lytic phage specific for *R. gnavus* may be used in some embodiments. Phage, including lytic phage, specific for *R. gnavus* (including *R. gnavus* group IBD strains) may be obtained from stool samples.

3. Probiotic Agent

At least one IBD therapy may comprise administering at least one probiotic agent. "Probiotic" therapy is intended to mean the administration of organisms and substances which help to improve the environment of the intestinal tract by inhibiting the disproportional growth of *R. gnavus* species or *R. gnavus* group IBD strains in the intestinal tract. For example, in healthy humans, the small intestine is colonized by lactobacilli (e.g., *L. acidophilus*), *Bifidobacterium*, gram-negative anaerobes, enterococci, and Enterobacteriaceae; the large intestine is colonized mainly by obligate anaerobes (e.g., *Bacteroides* sp., gram positive anaerobic cocci, *Clostridium* sp., Enterobacteriaceae (mainly *E. coli*), and enterococci. These bacteria produce substances which suppress harmful bacteria; for example, bifidobacteria produce lactic and acetic acid, decreasing the pH of the intestines. They can also activate macrophages, which also help suppress harmful bacteria. The best strains for supplementation are those that are typically permanent residents of the human intestinal tract and which do not produce toxins. Normal human intestinal flora are better adapted to the environment (bile acids, anaerobic conditions, etc.) of the human intestinal tract, and are more likely to survive and colonize the human intestinal tract.

In some embodiments, the at least one probiotic agent comprises one or more normal inhabitants of the human intestinal tract. For example, but not providing a comprehensive list, the least one probiotic agent may be chosen from *Bacteroides, Prevotella, Porphyromonas, Fusobacterium, Sutterella, Bilophila, Campylobacter, Wolinella, Butyrovibrio, Megamonas, Desulfomonas, Desulfovibrio, Bifidobacterium, Lactobacillus, Eubacterium, Actinomyces, Eggerthella, Coriobacterium, Propionibacterium, Bacillus, Peptostreptococcus, Peptococcus, Acidaminococcus, Ruminococcus, Megasphaera, Gaffkya, Coprocaccus, Veillonella, Sarcina, Clostridium, Aerococcus, Streptococcus, Enterococcus, Pediococcus, Micrococcus, Staphylococcus, Corynebacterium*, Enterobacteriaceae, Pseudomonadaceae, and mixtures thereof.

4. Lifestyle Modification

Lifestyle modifications may also be used as IBD treatment or a component of IBD treatment. At least one lifestyle modification may be chosen from stopping smoking, stopping isotretinoin use, stopping nonsteroidal anti-inflammatory medication use, and dietary modification, and at least one alternative medicine.

For example, dietary modifications may be chosen from iron supplements, B-12 supplements or shots, calcium supplements, vitamin D supplements, enteral nutrition, parenteral nutrition, a low-residue and/or low fiber diet, reducing dairy products, reducing lactose consumption, a low-fat diet, avoiding uncooked fruits and vegetables, reducing irritating foods (including reducing foods in the cabbage family (broccoli, cauliflower, cabbage), reducing nuts and seed, reducing corn and popcorn, reducing spicy foods, reducing alcohol, and reducing caffeine), eating smaller and more frequent meals, drinking more liquids, and taking a multivitamin. In some embodiments, at least one lifestyle modification is chosen from exercise, biofeedback, and regular relaxation and breathing exercises.

5. Alternative Medicine

In some embodiments, alternative medicine treatments may be used as IBD treatment or a component of IBD treatment. In some embodiments, the at least one alternative medicine comprises fish oil supplement, aloe vera supplement, turmeric or curcumin supplement, and acupuncture.

6. Surgery

Surgery may also play a role in IBD therapy. In some embodiments, the surgery is chosen from removing a bowel obstruction, repairing or removing ulcers, draining and/or repairing abscesses, repairing or removing fistulas, removing inflamed and/or narrowed portions of the gastrointestinal tract, proctocolectomy, and strictureplasty.

II. Diagnostic Methods

The methods of the invention include diagnostic applications. For example, indication of the presence and/or prevalence of *R. gnavus* IBD strain in a subject can be used prognostically to identify those subjects likely to have IBD, or diagnostically to identify the presence of IBD. Ongoing monitoring of the presence and/or prevalence of *R. gnavus* IBD strain in a subject during treatment of the subject can serve as a gauge of the efficacy of the treatment and/or the need for further treatment.

Thus, a method of diagnosing IBD in a human subject comprises: (a) determining from a gut microbiome sample whether the gut microbiome comprises *R. gnavus* and (b) diagnosing the subject as having IBD when *R. gnavus* is identified.

Diagnostic options include tests based on detection of those genes known to be associated with the species or strains for detection. Such tests include amplification of nucleic acids representing such genes (e.g., by PCR; specific hybridization assays (e.g., in situ hybridization; Northern, Southern, or dot blots; microarray hybridization, etc.); detection of the gene products themselves using, e.g., antibodies, (generated monoclonally, polyclonally, or derived from patients with high titers of such antibodies in ELISAs, sandwich assays, Western blots, or affinity chromatography; animal assays; laser mass spectroscopy, or any other methods known to those of skill in the art Samples can be obtained from fecal samples, blood, plasma, urine, saliva, cerebrospinal fluid, biopsy tissue, or any other patient source, and may be directly tested or after isolation of suspected causative agents.

Screening assays are based on detection of suspect organisms in the feces of patients using culture and microbiologic identification techniques, immunofluorescent techniques, genetic probes, laser mass spectroscopy, or other methods known in the art.

Further diagnostic information is obtained from a procedure chosen from at least one of colonoscopy, flexible sigmoidoscopy, upper endoscopy, capsule endoscopy, double-balloon endoscopy, x-ray, CT scan, MRI, and small bowel imaging.

Diagnosis, including all of the aspects described herein, may be used alone or in combination with therapy, as described herein.

III. Features Common to Both Therapeutic and Diagnostic Methods

In some embodiments, other features may be common to both therapeutic and diagnostic methods.

IBD includes a plurality of narrower conditions, including Crohn's disease or ulcerative colitis. Less common forms of IBD are also included, namely, collagenous colitis, lymphocytic colitis, diversion colitis, Behcet's disease, or indeterminate colitis.

R. gnavus (or R. gnavus group IBD) may have at least 5% relative abundance in the subject. In some embodiments, the relative abundance is much higher, including at least 10%, 20%, 30%, or 40% relative abundance in the subject. Because the relative abundance varies over time, these percentages include any one time point that has a qualifying relative abundance. The relative abundance need not average or maintain constantly over these figures.

More specifically, the strain of R. gnavus named R. gnavus group IBD is elevated in IBD patients as compared to heathy controls. The R. gnavus group IBD is characterized by a number of features including that (a) it comprises adherence-related genes, (b) it comprises genes involved in glycine-betaine transport, (c) it comprises at least one gene from Table 7 (whether at least one cluster 1 gene, at least one cluster 2 gene, at least one cluster 3 gene, and/or at least one cluster 4 gene or even up to all of the genes in Table 7), (d) is missing the Acetyl-CoA synthetase gene and/or the corrinoid iron-sulfur small subunit, (e) comprises genes for mucus utilization, (f) comprises at least one glycoside hydrolase gene (such as at least one gene identified in Table 9, for example at least one chosen from g000676, g001578, g001597, g002881, g002982, g003046, g003139, g003144, g003577, g003631, g004607, g005357, g006085, g006118, and g007627 (and optionally at least 2, 3, 4, 5, 6, 7, 8, 9, 10, 11, 12, 13, 14, or 15 of such genes).

In some embodiments, multiple samples of the subject's gut microbiome are obtained over time. In these embodiments, the relative abundance of R. gnavus may vary over time. In such embodiments, the relative abundance may differ between samples by at least 5%, 10%, 15%, 20%, 25%, or 30%.

Samples may be obtained for diagnosis or for identifying candidates for therapy from a variety of sources. First, the gut microbiome sample may be obtained from stool. Second, the gut microbiome sample may be obtained from a biopsy of the mucus lining of the gastrointestinal tract. The mucus lining may be obtained from the small intestine and/or the large intestine. Multiple sources of samples from one patient may be used and compared to each other or analyzed in parallel.

IV. Kits

Kits for detecting R. gnavus species and strains or their genetic markers, as detailed throughout this application, can be useful for the diagnosis of IBD. Kits can also provide benefit when evaluating the effectiveness of therapy in a given patient or when evaluating the effectiveness of a potential new therapy.

A kit to detect R. gnavus from a gut microbiome sample comprises (a) an agent for detecting R. gnavus and/or R. gnavus group IBD; and (b) optionally buffers and/or reaction solutions.

In some embodiments, the kit can detect R. gnavus group IBD.

In some embodiments, the agent for detecting R. gnavus and/or R. gnavus group IBD is chosen from: (a) at least one nucleic acid probe capable of hybridizing to a R. gnavus nucleic acid; (b) at least one primer pair for amplifying a R. gnavus nucleic acid; and (c) an antibody or antigen binding fragment thereof specific for R. gnavus.

In some embodiments, the R. gnavus nucleic acid is at least one of the genes in Table 7 or Table 9. In some embodiments, the R. gnavus nucleic acid is a 16S rRNA gene.

V. Definitions

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective treatment. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "eliminating" refers to the complete or nearly complete removal of R. gnavus species or at least one R.

*gnavus* group IBD strain from the gut microbiome of the subject. Nearly complete removal means a reduction of at least 95% of the species or strain from the gut microbiome.

The term "suppressing" refers to the reduction of *R. gnavus* species or at least one *R. gnavus* group IBD strain from the gut microbiome of the subject. This includes reduction by any significant amount to provide a clinical benefit (including reduction of at least 20%, 30%, 40%, 50%, 60%, 70%, 80%, or 90%).

EXAMPLES

Here, we used whole metagenome sequencing of a longitudinal cohort to characterize the taxonomic and functional differences in the gut microbiome of individuals with IBD compared to control subjects. Using this rich dataset, we related dysbiosis of IBD to how microbes handle oxidative stress. To quantify the microbial response to oxidative stress in IBD, we used literature searches to bin taxa by aerotolerance. We found a taxonomically diverse set of facultative anaerobes were increased in IBD. Notably, taxonomic profiling identified dramatic, but transient, increases in the relative abundance of *R. gnavus* in IBD often corresponding with inflammation. We identified an IBD-specific strain of *R. gnavus* with a distinct functional repertoire including genes exclusively present in IBD samples. Comparative genomic analysis of the *R. gnavus* genome revealed that this species likely occupies a mucogenic niche due to the absence of the essential gene of the acetogenesis pathway acetyl-CoA synthetase and the presence of mucus-degrading enzymes. These data show that massive increases in the abundance of mucus-utilizing, epithelial-associated strains of *R. gnavus* are a part of the dysbiotic consortia in IBD.

Example 1: Methods

A. Study Populations

1. Longitudinal Stool Study (LSS) Cohort

A subset of the PRISM cohort was selected for longitudinal analysis. A total of 15 IBD cases (9 CD, 5 UC, 1 indeterminate colitis) were enrolled in the longitudinal stool study. Three participants with gastrointestinal symptoms that tested negative for IBD were included as a control population. Enrollment in the study did not affect treatment. Stool samples were collected monthly, for up to 12 months. The first stool sample was taken after treatment had begun. Comprehensive clinical data for each of the participants was collected at each visit. At each collection, a subset of participants were interviewed to determine their disease activity index, the Harvey-Bradshaw index for CD participants and the simple clinical colitis activity index (SCCAI) for UC participants.

a. DNA and RNA Isolation

For the LSS cohort, DNA and RNA were extracted from stool using the AllPrep RNA/DNA Mini kit (Qiagen) with an enzymatic and mechanical lysis step. Lysozyme and proteinase K were added to frozen stool as described in RNA-protect Bacteria Reagent (Qiagen) handbook with a 10 min incubation at room temperature while vortexing every 2 min. Samples were resuspended in RLT buffer and 0.1 mm glass beads were added for mechanical lysis with bead beating on a Mini Bead beater-8 (BioSpec Products) on the homogenize setting for 3 min. Debris was removed by two sequential centrifugation steps at maximum speed for 5 min. Supernatant was transferred to a QIAshredder spin column (Qiagen) and homogenized lysate was added to the AllPrep spin column for DNA and RNA extraction using QIAGEN protocols.

b. Fecal Calprotectin

Fecal calprotectin (FCP) was assayed for each stool sample with the Eagle Biosciences Calprotectin Enzyme-Linked Immunoabsorbent Assay (ELISA) kit using standard protocols.

2. STiNKi Cohort

To increase the number of participants in our analysis, we choose to include a subset of the pediatric cohort, identified herein as STiNKi, was selected for whole metagenome sequencing including 5 individuals with UC and 9 healthy controls. All selected UC cases were categorized as non-responders to treatment. Shaw et al., Dysbiosis, Inflammation, and Response to Treatment: a Longitudinal Study of Pediatric Subjects with Newly Diagnosed Inflammatory Bowel Disease, Genome Medicine 8:75 (2016). Stool samples were collected approximately monthly for up to 10 months. The first sample from participants in the STiNKi cohort is before treatment started, and subsequent samples are after treatment started. Stool collection and DNA extraction methods are detailed in Shaw et al. 2016.

B. STiNKi DNA and RNA Isolation

Total Nucleic Acid was extracted via the Chemagic MSM I with the Chemagic DNA Blood Kit-96 from Perkin Elmer. This kit combines a chemical and mechanical lysis with magnetic bead-based purification. Prior to extraction on the MSM-I, TE buffer, Lysozyme, Proteinase K, and RLT Buffer with beta-mercaptoethanol were added to each stool sample. The stool lysate solution was vortexed to mix. Samples were then placed on the MSM I unit. The following steps were automated on the MSM I. M-PVA Magnetic Beads were added to the stool lysate solution and vortexed to mix. The bead-bound Total Nucleic Acid (TNA) was then removed from solution via a 96-rod magnetic head and washed in three Ethanol-based wash buffers. The beads were then washed in a final water wash buffer. Finally, the beads were dipped in elution buffer to re-suspend the DNA sample in solution. The beads were then removed from solution, leaving purified TNA eluate. The eluate was then split into two equal volumes, one meant for DNA the other for RNA. SUPERase-IN solution was added to the DNA samples, the reaction was cleaned up using AMPure XP SPRI beads. DNase was added to the RNA samples, and the reaction was cleaned up using AMPure XP SPRI beads. DNA samples were quantified using a fluorescence-based PicoGreen assay. RNA samples were quantified using a fluorescence-based RiboGreen assay. RNA quality was assessed via smear analysis on the Caliper LabChip GX.

1. Validation Cohorts

Data from an IBD study by Lewis et al. was downloaded from the NCBI SRA for use as an IBD validation cohort. Lewis et al., Inflammation, Antibiotics, And Diet as Environmental Stressors of the Gut Microbiome in Pediatric Crohn's Disease, Cell Host Microbe 18(4):489-500 (2015). 80 samples from the HMP for use as a healthy validation cohort. The Human Microbiome Project Consortium, Structure, Function and Diversity of the Healthy Human Microbiome, Nature 486(7402):207-214 (2012).

Thus, as a summary, Table 1 provides the following number of individuals and samples used in the analysis in the examples.

TABLE 1

Summary of Samples and Individuals

| Samples | Individuals (n) | Samples (n) |
|---|---|---|
| LSS IBD | 20 | 190 |
| LSS Healthy control | 12 | 76 |
| Lewis et al. IBD | 86 | 306 |
| Lewis et al. Healthy control | 25 | 25 |
| HMP Healthy control | 80 | 80 |

C. Metagenomic WGS Analysis

The whole metagenome data was trimmed and human reads were filtered using KneadData using the default parameters. Community composition was calculated with MetaPhlan2 using the default settings. Functional and pathway composition was calculated with HUMANn2 using the UniRef90 database with default settings. Differentially-abundance species and pathways were identified using MaAsLin. Strain-level analysis was performed using PanPhlan with the default parameters.

D. Binning by Aerotolerance Methods

The output from the MetaPhlAn2 analysis was binned by aerotolerance based on relative abundance. To define differential bins of aerotoerance, we started with the list assembled by Albenberg et al and expanded for abundant genera in our samples. Alberberg et al., Correlation Between Intraluminal Oxygen Gradient and Radial Partitioning of Intestinal Microbiota in Humans and Mice, Gastroenterology 147(5):1055-1063 (2014).

E. Pangenome Analysis with PanPhlAn

Pangenome analysis was performed with PanPhlan, which determines the presence or absence of all the genes of an organism's pangenome in metagenomic samples. PanPhlAn requires approximately 1-2× coverage of the genome of the species of interest to accurately determine presence or absence of the genes in the pangenome. Due to the low coverage of many of the differentially abundant species in health or IBD, longitudinal samples from each individual were pooled into a single sample. This allowed for pangenome analysis on many low-abundance species such as R. gnavus.

1. Generation of a Pangenome Database for R. Gnavus

Only 3 R. gnavus genomes were integrated into the default pangenome database supplied with PanPhlAn. An additional 3 R. gnavus genomes were available from the NCBI. However, all 6 genomes were isolates from healthy humans or cows. We choose R. gnavus for in-depth analysis because it has been consistently identified as more abundant in individuals with IBD across multiple studies. To determine if there were R. gnavus strains specific to IBD, we performed a metagenomic assembly on a sample with extremely low diversity containing 41.6 percent R. gnavus by relative abundance, p8808_mo11. The next most abundant species in this sample are E. coli and Clostridium nexile which are both around 9 percent relative abundance. Therefore, this sample presents an excellent opportunity for assembly of an R. gnavus genome because R. gnavus is by far the most abundant species present. We performed metagenomic assembly on sample p8808_mo11 with the SPAdes assembler using the default parameters. To select R. gnavus contigs from the resulting assembly, we employed two criteria: coverage, and presence of known R. gnavus genes. First, we compared the default R. gnavus pangenome database with the metagenomic contigs using BLASTn using the parameter e-value 1 e-30 and identified contigs with more than 20 R. gnavus genes. Using the SPAdes coverage output, we estimated the range of coverage expected for R. gnavus contigs. Based on this estimation, we choose contigs with a minimum of 60× coverage. The further refine the selection of R. gnavus contigs, from the subset of contigs with greater than 60× coverage, we selected contigs with at least two known R. gnavus genes using BLASTn with an evalue of 1e-30. The resulting assembly contained 69 contigs with an N50 length of 62,637 bp. Using the PanPhlAn pangenome generation tool, we constructed a custom pangenome database for R. gnavus integrating the 6 genomes from the NCBI and the additional genome generated by metagenomic assembly. The custom R. gnavus pangenome was then used for all additional pangenome analysis.

Besides R. gnavus, we ran pangenome analysis with PanPhlAn for many additional abundant species that are differentially abundant in IBD compared to healthy controls including F. prausnitzii and R. torques, using the sensitive parameters for PanPhlAn.

F. Annotation of Wood-Ljungdahl Pathway in Blautia Species

Downloaded proteins for each genome from the NCBI, use the B. hydrogenotrophica genes as query for BLASTp against the proteins for each gene in the pathway. Results were then manually curated.

In other Blautia species such as B. producta and B. obeum, the hits to acetyl-CoA synthetase were highly significant (blastp e-value 0.0), while the best hit in R. gnavus was highly insignificant in comparison (blastp e-value 0.1) and corresponded to an ATPase. Co-occurrence of both acetyl-CoA synthetase and corrinoid is required for a complete Wood-Ljungdahl pathway. Pierce et al., The Complete Genome Sequence of Moorella thermoacetica (f. Clostridium thermaceticum), Environ Microbiologu 10(10): 2550-2573 (2008); Rey et al., Dissecting the in Vivo Metabolic Potential of Two Human Gut Acetogens, The Journal of Biological Chemistry 285(29):22082-22090 (2010)

Example 2: Results

A. Study Design

IBD is characterized by relapsing inflammation followed by periods of remission. To capture intra-individual variation in the gut microbiome of individuals with IBD, we designed a prospective cohort study called the longitudinal stool study (LSS). The LSS cohort included 20 individuals with IBD, and 12 controls. Stool samples were collected monthly, for up to 12 months, where the first stool sample was taken after treatment had begun. Previous 16S rRNA gene-based IBD studies identified differentially-abundant genera, and imputed differentially-abundant pathways based on tools such as PICRUSt that impute function based on taxonomy. To improve the taxonomic resolution and annotation of the functional potential, we performed whole metagenomic sequencing (WMS) for 266 longitudinal samples.

To validate our findings with other IBD cohorts we used 331 WMS samples from Lewis et al., a longitudinal study of the microbiome of individuals with CD starting either a defined formula diet or anti-TNF therapy with four time points, 0, 1, 4, and 8 weeks, as a validation cohort. Lewis et al., Inflammation, Antibiotics, and Diet as Environmental Stressors of the Gut Microbiome in Pediatric Crohn's Disease, Cell Host Microbe 18(4):486-500, doi:10.1016/j.chom.2015.09.008 (2015). We additionally used 80 stool samples from the Human Microbiome Project (I-IMP) as a source of additional healthy individuals. The Human Microbiome Project Consortium, Structure, Function and Diversity of the Healthy Human Microbiome, Nature 486(7402): 207-214 (2012).

B. Differentially Abundant Species and Pathways in the IBD Gut

Figure 1B:
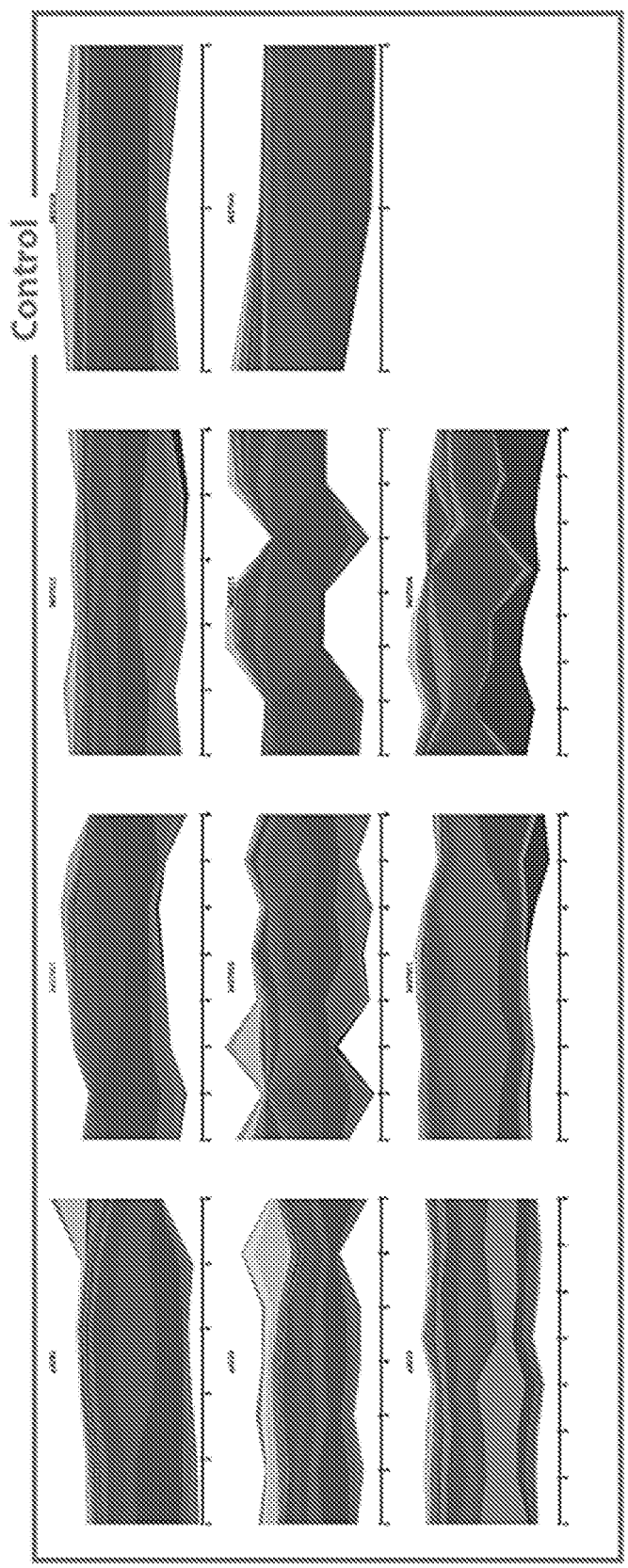

Taxonomic and functional profiling of WMS data were performed using MetaPhlan2 and HUMAnN2 respectively (FIG. 1). Truong et al., MetPhlAn2 for Enhanced Metagenomic Taxonomic Profiling, Nature Methods 12:902-903 (2015). Differentially-abundance species and pathways were identified using MaAsLin. Morgan et al., Dysfunction of the Intestinal Microbiome in Inflammatory Bowel Disease and Treatment, Genome Biology 13:R79 (2012). We identified 24 differentially abundant (p<0.05, q<0.25) species between IBD patients and control individuals, 9 of which were also differentially abundant in the same direction in the validation cohort (Tables 1 and 2). The relative abundance of 15 species was increased in IBD. Five of these species (4 Streptococcus species and Haemophilus parainfluenzea) are typical facultatively anaerobic colonizers of the oral microbiome, and are relatively rare in the gut. Several of the species whose relative abundance decreased in IBD are consistent with previous observations, including the obligate anaerobes Faecalibacterium prausnitzii, and Ruminococcus bromii. Lewis et al., Inflammation, Antibiotics, and Diet as Environmental Stressors of the Gut Microbiome in Pediatric Crohn's Disease, Cell Host Microbe 18(4):486-500, doi: 10.1016/j.chom.2015.09.008 (2015).

TABLE 2

Differentially abundant species (MaAsLin) from the LSS cohort

| Feature | Coefficient | P-value | Q-value |
|---|---|---|---|
| Streptococcus_parasanguinis | 0.017 | 0.0003 | 0.0350 |
| Streptococcus_salivarius | 0.021 | 0.0012 | 0.0464 |
| Alistipes_putredinis | −0.129 | 0.0012 | 0.0464 |
| Clostridium_leptum | −0.015 | 0.0019 | 0.0464 |
| Odoribacter_splanchnicus | −0.048 | 0.0022 | 0.0464 |
| Alistipes_finegoldii | −0.014 | 0.0022 | 0.0464 |
| Clostridium_scindens | 0.002 | 0.0031 | 0.0490 |
| Blautia_producta | 0.005 | 0.0031 | 0.0490 |
| Streptococcus_sanguinis | 0.004 | 0.0069 | 0.0963 |
| Eubacterium_siraeum | −0.055 | 0.0079 | 0.0990 |
| Clostridium_clostridioforme | 0.010 | 0.0126 | 0.1433 |
| Lachnospiraceae_bacterium_5_1_57FAA | 0.007 | 0.0171 | 0.1699 |
| Coprobacillus_unclassified | 0.009 | 0.0177 | 0.1699 |
| Ruminococcus_bromii | −0.062 | 0.0216 | 0.1837 |
| Faecalibacterium_prausnitzii | −0.108 | 0.0226 | 0.1837 |
| Eubacterium_ventriosum | −0.021 | 0.0235 | 0.1837 |
| Ruminococcus_gnavus | 0.036 | 0.0265 | 0.1945 |
| Akkermansia_muciniphila | −0.004 | 0.0302 | 0.2096 |
| Eggerthella_lenta | 0.007 | 0.0336 | 0.2096 |
| Haemophilus_parainfluenzae | 0.007 | 0.0340 | 0.2096 |
| Streptococcus_vestibularis | 0.005 | 0.0352 | 0.2096 |
| Clostridium_asparagiforme | 0.007 | 0.0401 | 0.2277 |
| Clostridium_bartlettii | 0.010 | 0.0480 | 0.2499 |
| Clostridium_ramosum | 0.004 | 0.0480 | 0.2499 |

TABLE 3

Differentially abundant species (MaAsLin) from Lewis et al. validation cohort

| Feature | Coefficient | P-value | Q-value |
|---|---|---|---|
| Bacteroidales_bacterium_ph8 | −0.028 | 8.81E−08 | 0.0000 |
| Ruminococcus_bromii | −0.080 | 1.35E−06 | 0.0001 |
| Roseburia_hominis | −0.013 | 1.82E−06 | 0.0001 |
| Eubacterium_hallii | −0.034 | 4.07E−06 | 0.0001 |
| Eubacterium_eligens | −0.060 | 2.48E−05 | 0.0006 |
| Eubacterium_rectale | −0.075 | 7.09E−05 | 0.0015 |
| Alistipes_indistinctus | −0.012 | 9.89E−05 | 0.0016 |
| Clostridium_leptum | −0.022 | 0.0001 | 0.0016 |
| Dorea_longicatena | −0.024 | 0.0004 | 0.0061 |
| Coprococcus_catus | −0.011 | 0.0006 | 0.0077 |
| Parabacteroides_merdae | −0.058 | 0.0007 | 0.0077 |
| Odoribacter_splanchnicus | −0.043 | 0.0007 | 0.0077 |
| Eubacterium_ramulus | −0.011 | 0.0009 | 0.0085 |
| Alistipes_shahii | −0.030 | 0.0011 | 0.0096 |
| Alistipes_finegoldii | −0.019 | 0.0018 | 0.0151 |
| Escherichia_unclassified | 0.020 | 0.0019 | 0.0151 |
| Ruminococcus_obeum | −0.018 | 0.0023 | 0.0163 |
| Escherichia_coli | 0.053 | 0.0024 | 0.0163 |
| Roseburia_inulinivorans | −0.013 | 0.0025 | 0.0163 |
| Streptococcus_parasanguinis | 0.027 | 0.0039 | 0.0238 |
| Collinsella_aerofaciens | −0.015 | 0.0040 | 0.0238 |
| Subdoligranulum_unclassified | −0.073 | 0.0052 | 0.0299 |
| Lachnospiraceae_bacterium_5_1_63FAA | −0.013 | 0.0069 | 0.0373 |
| Dorea_formicigenerans | −0.011 | 0.0071 | 0.0373 |
| Eubacterium_ventriosum | −0.021 | 0.0095 | 0.0476 |
| Ruminococcus_gnavus | 0.068 | 0.0098 | 0.0476 |
| Barnesiella_intestinihominis | −0.046 | 0.0105 | 0.0490 |
| Bacteroides_dorei | −0.083 | 0.0169 | 0.0760 |
| Alistipes_putredinis | −0.075 | 0.0223 | 0.0970 |
| Parabacteroides_unclassified | −0.039 | 0.0243 | 0.1022 |
| Bacteroides_uniformis | −0.074 | 0.0260 | 0.1059 |
| Eggerthella_unclassified | 0.010 | 0.0312 | 0.1228 |
| Coprococcus_comes | −0.015 | 0.0385 | 0.1470 |
| Streptococcus_salivarius | 0.023 | 0.0399 | 0.1470 |
| Anaerostipes_hadrus | −0.006 | 0.0414 | 0.1470 |
| Roseburia_intestinalis | −0.042 | 0.0428 | 0.1470 |
| Granulicatella_unclassified | 0.003 | 0.0441 | 0.1470 |
| Ruminococcus_sp_5_1_39BFAA | −0.016 | 0.0448 | 0.1470 |
| Bilophila_unclassified | −0.011 | 0.0463 | 0.1470 |
| Oscillibacter_unclassified | −0.016 | 0.0467 | 0.1470 |

We also identified 34 differentially abundant pathways (Table 4) and 178 differentially abundant KEGG orthology groups (KOs) (Table 5). The most significant differentially-abundant pathways were isoprene biosynthesis followed by the methylerythritol phosphate pathway. Both pathways are involved in the biosynthesis of terpenoids, which currently have unknown functions in the gut. Several differentially abundant pathways are consistent with previous findings regarding differential abundance of amino acid biosynthesis pathways, including isoleucine, arginine and lysine biosynthesis. Morgan et al., Dysfunction of the Intestinal Microbiome in Inflammatory Bowel Disease and Treatment, Genome Biology 13:R79 (2012).

TABLE 4

Differentially abundant MetaCyc pathways

| Feature | Coefficient | P-value | Q-value |
|---|---|---|---|
| PWY__6270__isoprene__biosynthesis__I | 0.0041 | 7.80E-05 | 0.005 |
| PWY__7560__methylerythritol__phosphate__pathway__II | 0.0039 | 8.38E-05 | 0.005 |
| PWY__5101__L__isoleucine__biosynthesis__II | -0.0041 | 0.00011 | 0.005 |
| PWY66__409__superpathway__of__purine__nucleotide__salvage | 0.0034 | 0.00015 | 0.005 |
| RIBOSYN2__PWY__flavin__biosynthesis__I__bacteria__and__plants__ | -0.0040 | 0.00023 | 0.007 |
| PANTO__PWY__phosphopantothenate__biosynthesis__I | -0.0022 | 0.00075 | 0.018 |
| PWY__5695__urate__biosynthesis__inosine__5__pliosphate__degradation | -0.0024 | 0.00087 | 0.018 |
| GLUTORN__PWY__L__ornithine__biosynthesis | 0.0028 | 0.00200 | 0.037 |
| PWY__5973__cis__vaccenate__biosynthesis | -0.0036 | 0.00246 | 0.039 |
| PWY__7663__gondoate__biosynthesis__anaerobic__ | -0.0037 | 0.00266 | 0.039 |
| PWY__7383__anaerobic__energy__metabolism__invertebrates__cytosol__ | -0.0025 | 0.00338 | 0.044 |
| PWY__1042__glycolysis__IV__plant__cytosol__ | -0.0031 | 0.00354 | 0.044 |
| ARGSYNBSUB__PWY__L__arginine__biosynthesis__II__acetyl__cycle__ | 0.0031 | 0.00383 | 0.044 |
| PWY0__1297__superpathway__of__purine__deoxyribonucleosides__degradation | 0.0021 | 0.00438 | 0.044 |
| PWY__6703__preQ0__biosynthesis | -0.0033 | 0.00456 | 0.044 |
| PWY__5659__GDP__mannose__biosynthesis | -0.0025 | 0.00478 | 0.044 |
| PWY__6936__seleno__amino__acid__biosynthesis | 0.0025 | 0.00575 | 0.050 |
| 1CMET2__PWY | -0.0032 | 0.00610 | 0.050 |
| GLUCUROCAT__PWY__superpathway__of__beta__D__glucuronide__and__D__glucuronate__degradation | -0.0026 | 0.00695 | 0.054 |
| ARGSYN__PWY__L__arginine__biosynthesis__I__via__L__ornithine__ | 0.0030 | 0.00810 | 0.060 |
| PYRIDOXSYN__PWY__pyridoxal__5__phosphate__biosynthesis__I | -0.0036 | 0.00871 | 0.061 |
| PWY__6385__peptidoglycan__biosynthesis__III__mycobacteria__ | -0.0018 | 0.01011 | 0.066 |
| GALACT__GLUCUROCAT__PWY__superpathway__of__hexuronide__and__hexuronate__degradation | -0.0025 | 0.01045 | 0.066 |
| ARGININE__SYN4__PWY__L__ornithine__de__novo__biosynthesis | -0.0038 | 0.01079 | 0.066 |
| PWY__3841__folate__ transformations__II | -0.0029 | 0.01166 | 0.066 |
| PWY__7400__L__arginine__biosynthesis__IV__archaebacteria__ | 0.0030 | 0.01177 | 0.066 |
| GALACTUROCAT__PWY__D__galacturonate__degradation__I | -0.0024 | 0.01207 | 0.066 |
| PWY__7242__D__fructuronate__degradation | -0.0024 | 0.01471 | 0.074 |
| PWY__5177__glutaryl__CoA__degradation | -0.0022 | 0.01491 | 0.074 |
| UDPNAGSYN__PWY__UDP__N__acetyl__D__glucosamine__biosynthesis__I | 0.0024 | 0.01510 | 0.074 |
| THISYNARA__PWY__superpathway__of__thiamin__diphosphate__biosynthesis__III__eukaryotes__ | -0.0020 | 0.01768 | 0.084 |
| PWY__6168__flavin__biosynthesis__III__fungi__ | -0.0026 | 0.02010 | 0.093 |
| ANAGLYCOLYSIS__PWY__glycolysis__III__from__glucose__ | -0.0019 | 0.02153 | 0.095 |
| PWY__2942__L__lysine__biosynthesis__III | -0.0021 | 0.02177 | 0.095 |

TABLE 5

The 50 most significant differentially abundant KOs in IBD subject samples compared to healthy subject samples from MaAsLin

| Feature | Coefficient | P. value | Q. value | Feature description |
|---|---|---|---|---|
| K01879 | 0.31 | 2.15E-07 | 0.00026 | glycyl-tRNA synthetase beta chain |
| K06286 | 0.42 | 3.96E-07 | 0.00026 | hypothetical |
| K03739 | 0.49 | 8.35E-07 | 0.00033 | Amp resistance |
| K18216 | 0.42 | 1.00E-06 | 0.00033 | tet transporter |
| K01641 | 0.56 | 2.60E-06 | 0.00068 | Ketone body biosynthesis |
| K00694 | 0.57 | 4.19E-06 | 0.00092 | cellulose synthase |
| K07778 | 0.55 | 5.42E-06 | 0.00096 | two-component system, NarL family, sensor histidine kinase DesK |
| K00687 | 0.43 | 6.29E-06 | 0.00096 | penicillin-binding protein 2B |
| K05845 | 0.24 | 7.28E-06 | 0.00096 | osmoprotectant transport system substrate-binding protein |
| K07004 | 0.51 | 7.30E-06 | 0.00096 | uncharacterized |
| K18692 | 0.48 | 1.03E-05 | 0.00123 | ATP-dependent RNA helicase CshB |
| K01274 | 0.42 | 1.16E-05 | 0.00123 | D-alanyl-D-alanine dipeptidase |
| K05846 | 0.22 | 1.24E-05 | 0.00123 | osmoprotectant transport system permease protein |
| K06948 | 0.64 | 1.40E-05 | 0.00123 | 30S ribosome assembly GTPase |
| K01220 | 0.42 | 1.55E-05 | 0.00123 | 6-phospho-beta-galactosidase |
| K14982 | 0.39 | 1.59E-05 | 0.00123 | two-component system, OmpR family, sensor histidine kinase CiaH |
| K08168 | 0.40 | 1.68E-05 | 0.00123 | tetB |
| K18217 | 0.37 | 1.68E-05 | 0.00123 | tet resistance |
| K16169 | 0.48 | 3.19E-05 | 0.00220 | xanthine permease |
| K01361 | 0.38 | 3.46E-05 | 0.00228 | lactocepin |
| K19355 | -0.45 | 4.38E-05 | 0.00274 | mannan endo-1,4-beta-mannosidase |
| K00841 | 0.52 | 5.42E-05 | 0.00324 | aminotransferase |
| K07652 | 0.47 | 5.99E-05 | 0.00342 | two-component system, OmpR family, sensor histidine kinase VicK |
| K15921 | -0.42 | 6.61E-05 | 0.00360 | arabinoxylan arabinofuranohydrolase |
| K03367 | 0.41 | 6.84E-05 | 0.00360 | D-alanine--poly(phosphoribitol) |
| K03346 | 0.46 | 7.32E-05 | 0.00370 | DNAb |

TABLE 5-continued

The 50 most significant differentially abundant KOs in IBD subject
samples compared to healthy subject samples from MaAsLin

| Feature | Coefficient | P. value | Q. value | Feature description |
|---|---|---|---|---|
| K03740 | 0.43 | 8.37E−05 | 0.00408 | D-alanine transfer protein |
| K05363 | 0.48 | 1.06E−04 | 0.00496 | serine/alanine adding enzyme |
| K00105 | 0.26 | 1.18E−04 | 0.00536 | alpha-glycerophosphate oxidase |
| K03342 | 0.34 | 1.37E−04 | 0.00592 | para-aminobenzoate synthetase |
| K05362 | 0.35 | 1.40E−04 | 0.00592 | Peptidoglycan biosynthesis |
| K05988 | 0.34 | 1.72E−04 | 0.00706 | dextranase |
| K13732 | 0.37 | 1.91E−04 | 0.00763 | fibronectin-binding protein A |
| K01615 | 0.23 | 1.97E−04 | 0.00763 | Butanoate metabolism |
| K03693 | 0.32 | 2.48E−04 | 0.00931 | penicillin-binding protein |
| K01281 | 0.29 | 2.55E−04 | 0.00931 | X-Pro dipeptidyl-peptidase |
| K02022 | −0.53 | 2.62E−04 | 0.00931 | HlyD family secretion protein |
| K12998 | 0.36 | 3.34E−04 | 0.01147 | glucosyltransferase |
| K05020 | 0.37 | 3.40E−04 | 0.01147 | glycine betaine transporter |
| K07706 | 0.37 | 3.50E−04 | 0.01150 | two-component system, AgrA family, sensor histidine kinase AgrC |
| K11198 | 0.21 | 4.00E−04 | 0.01224 | PTS system, 2-O-A-mannosyl-D-glycerate-specific IIA component |
| K11199 | 0.21 | 4.00E−04 | 0.01224 | PTS system, 2-O-A-mannosyl-D-glycerate-specific IIB component [EC: 2.7.1.195] |
| K11200 | 0.21 | 4.00E−04 | 0.01224 | PTS system, 2-O-A-mannosyl-D-glycerate-specific IIC component |
| K08166 | 0.35 | 4.53E−04 | 0.01355 | MFS transporter, DHA2 family, methylenomycin A resistance protein |
| K08643 | 0.34 | 5.29E−04 | 0.01545 | zinc metalloprotease ZmpB |
| K00158 | 0.30 | 6.36E−04 | 0.01818 | pyruvate oxidase |
| K09698 | 0.26 | 7.90E−04 | 0.02209 | nondiscriminating glutamyl-tRNA synthetase |
| K02575 | 0.26 | 8.41E−04 | 0.02303 | Nitrogen metabolism |
| K07267 | −0.37 | 9.33E−04 | 0.02504 | porin |
| K00720 | 0.41 | 1.03E−03 | 0.02703 | ceramide glucosyltransferase |

One notable difference between IBD and controls was the significant increase of K01361, encoding lactocepin, in IBD. Lactocepin is a protease that degrades IP-10, a proinflammatory chemokine involved in recruiting T cells to sites of inflammation. Von Schillde et al., Lactocepin Secreted by *Lactobacillus* Exerts Anti-Inflammatory Effects by Selectively Degrading Proinflammatory Chemokines, Clel Host & Microbe 11:387-396 (2012). In the mouse model of colitis, administration of lactocepin-secreting *Lactobacillus* species reduced inflammation by normalizing the levels of IP-10. Von Schillde et al. (2012). The increase of the genes for this anti-inflammatory molecule in IBD is unexplained.

C. Oxidative Stress in the IBD Gut Microbiome

As previously observed (Morgan et al., Dysfunction of the Intestinal Microbiome in Inflammatory Bowel Disease and Treatment, Genome Biology 13:R79 (2012); Ballal et al., Host Lysozyme-mediated Lysis of *Lactococcus lactis* Facilitates Delivery of Colitis-attenuating Superoxide Dismutase to Inflamed Colons, Proc Natl Acad Sci USA 112(25):7803-7808 (2015)), one of the main functional changes of the gut microbiome in IBD is the increased abundance of pathways involved in microbial metabolic handling of redox stress. Here, we found that glycine, which is involved in the biosynthesis of glutathione, a key antioxidant, was the most significantly increased KO in IBD. Furthermore, many species with increased abundance in IBD are facultative anaerobes, which are generally rare in the adult gut. The Human Microbiome Project Consortium, Structure, Function and Diversity of the Healthy Human Microbiome, Nature 486 (7402):207-214 (2012). Based on these observations, we specifically examined the response of the gut microbiome to oxidative stress in IBD.

D. The IBD Gut Microbiome is Enriched for Taxonomically Diverse Facultative Anaerobes To determine how the increased oxidative stress of the IBD gut shapes the composition of the gut microbiome, we binned the genera of the gut microbiome by their ability to respond to oxidative stress rather than by taxonomy. Using the list compiled by Albenberg et al. (Correlation Between Intraluminal Oxygen Gradient and Radial Partitioning of Intestinal Microbiota in Humans and Mice, Gastroenterology, 147(5):1055-1063 (2014)) as a starting point, and expanding to additional abundant genera in our data based on literature searches, we binned genera into three categories based on their ability to respond to oxidative stress: facultative anaerobes, aerotolerant anaerobes, and obligate anaerobes.

Figure 2A:
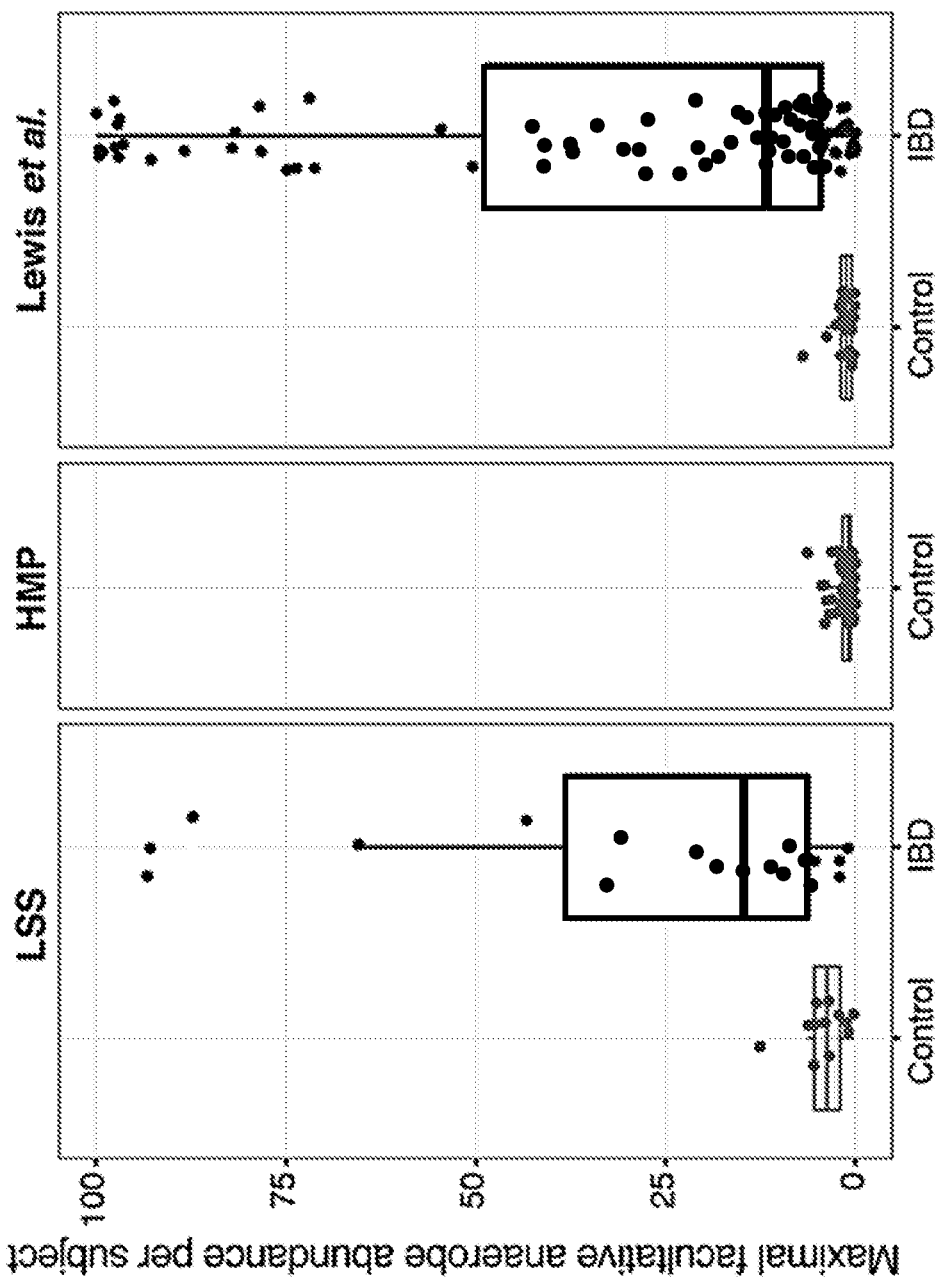
FIGS. 2A-H provide graphs showing the differential abundance of facultative anaerobes (and oxidative stress pathways) in samples from IBD and control patients.
Figure 2B:
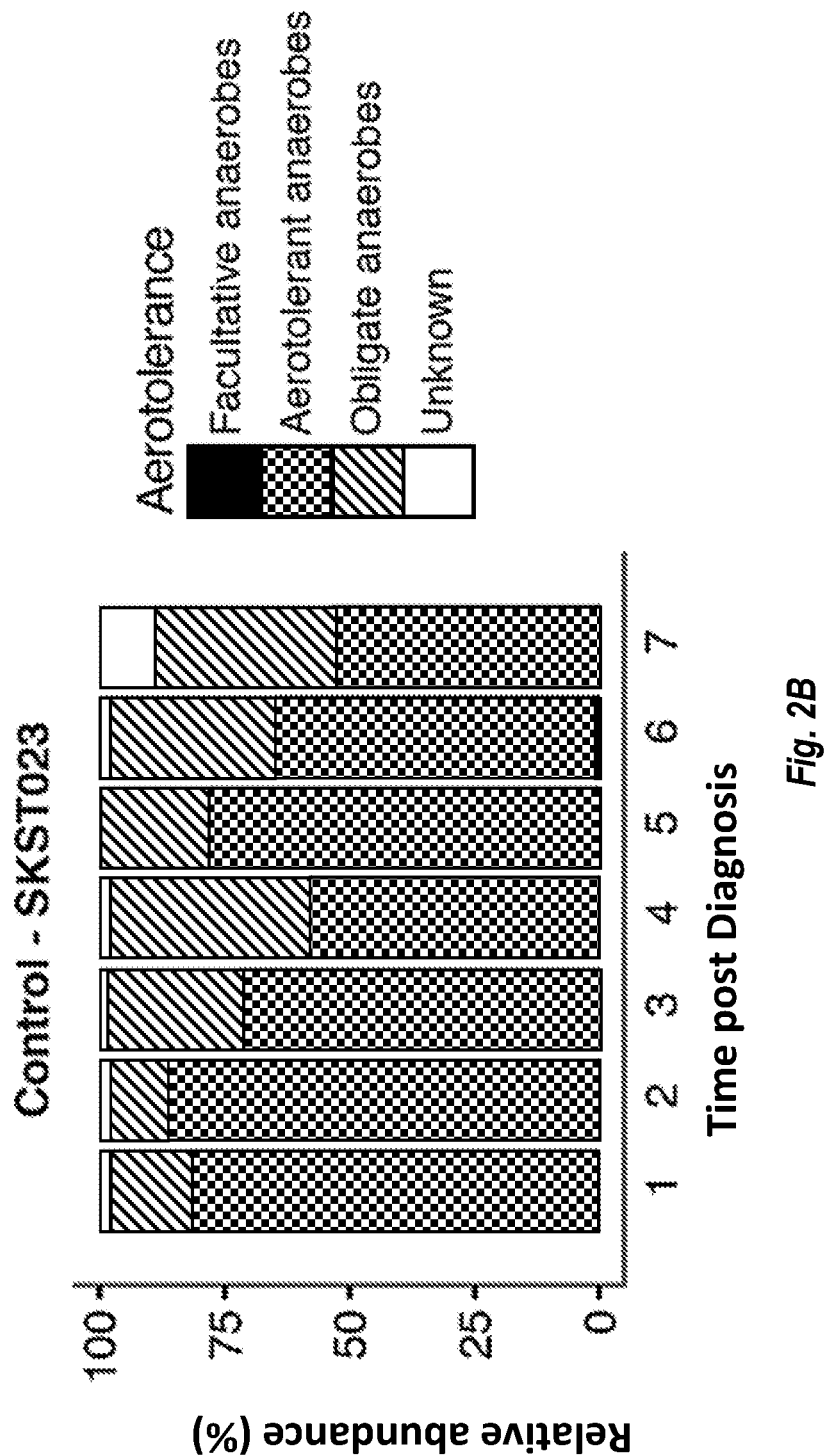
Figure 2C:
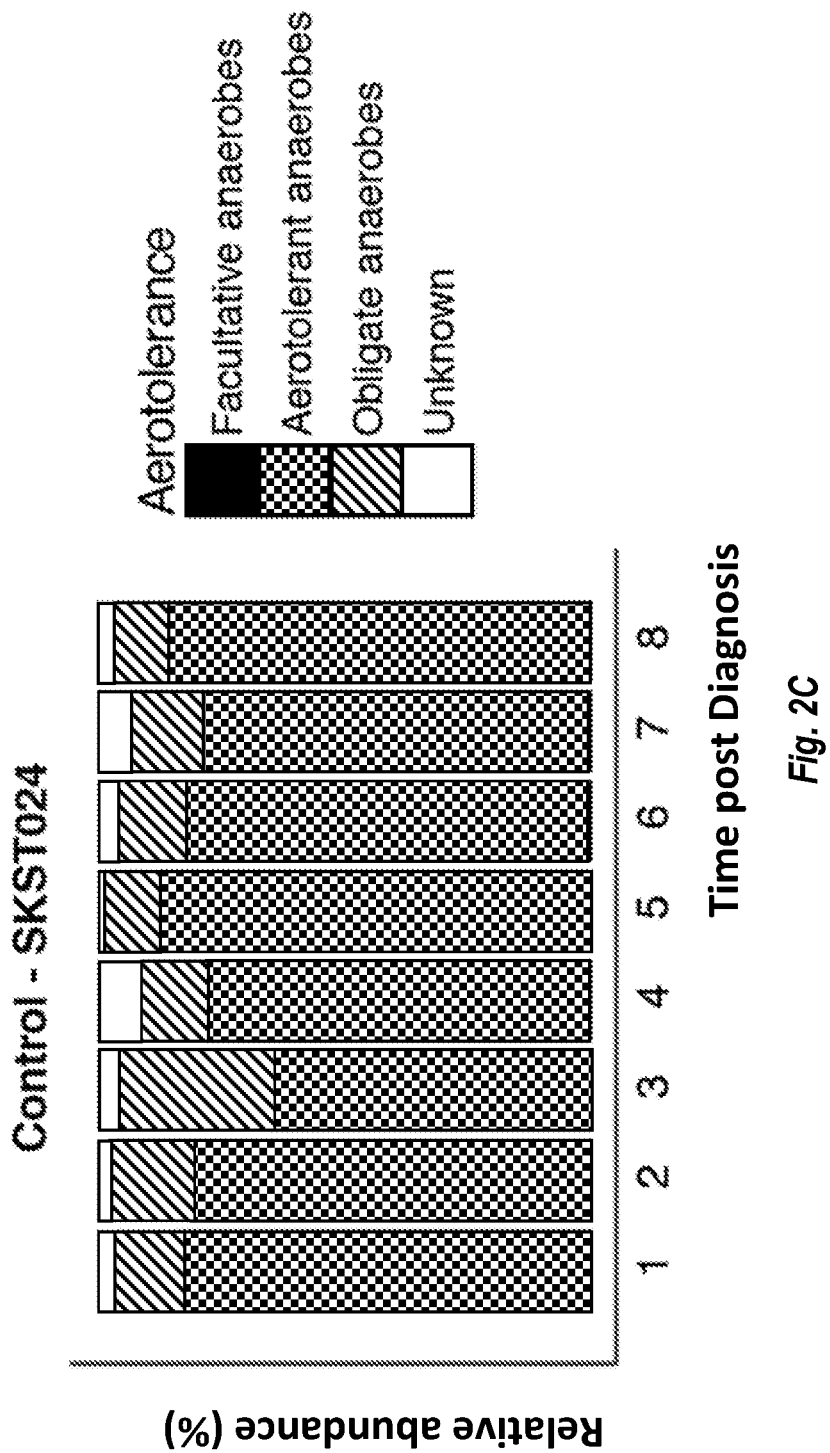
Figure 2D:
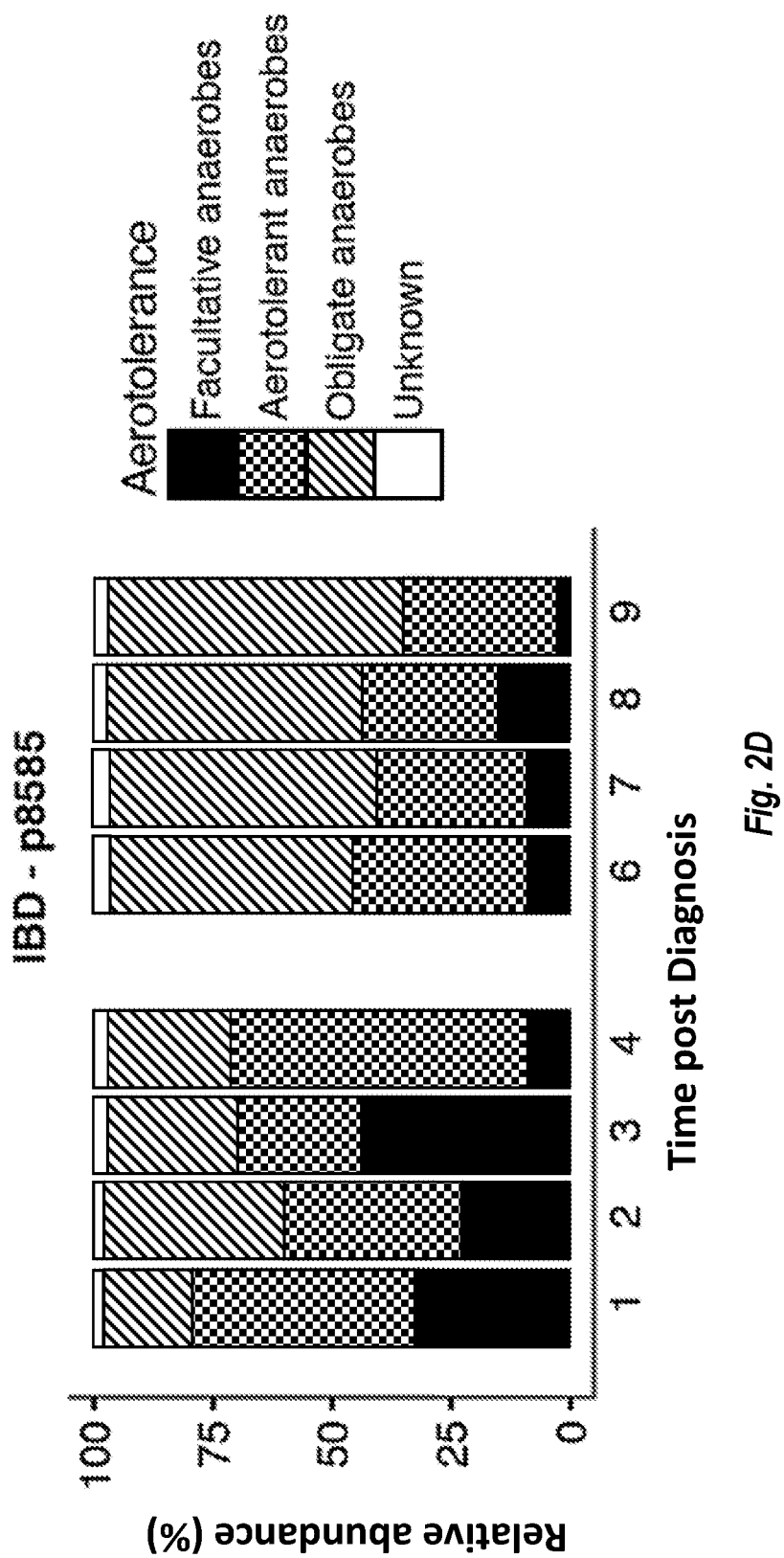
Figure 2E:
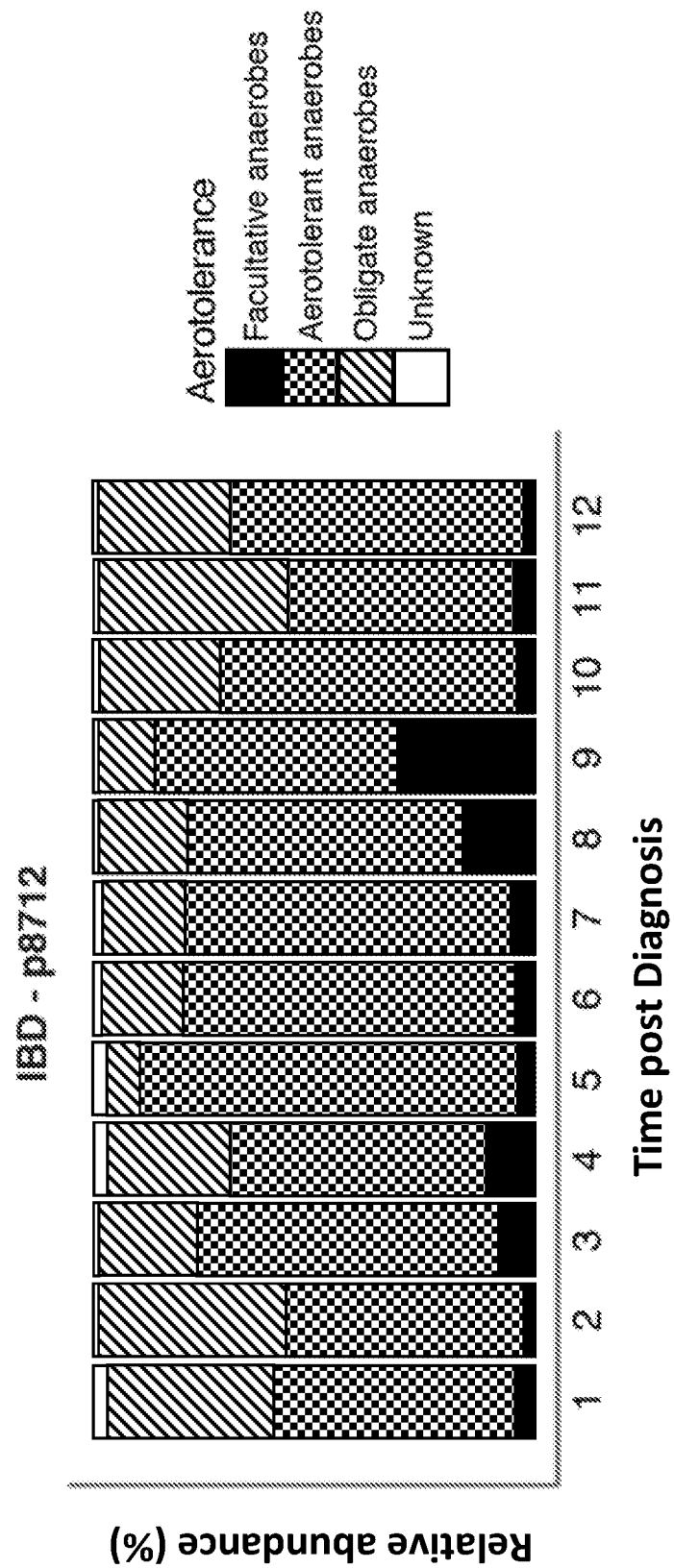
Figure 2F:
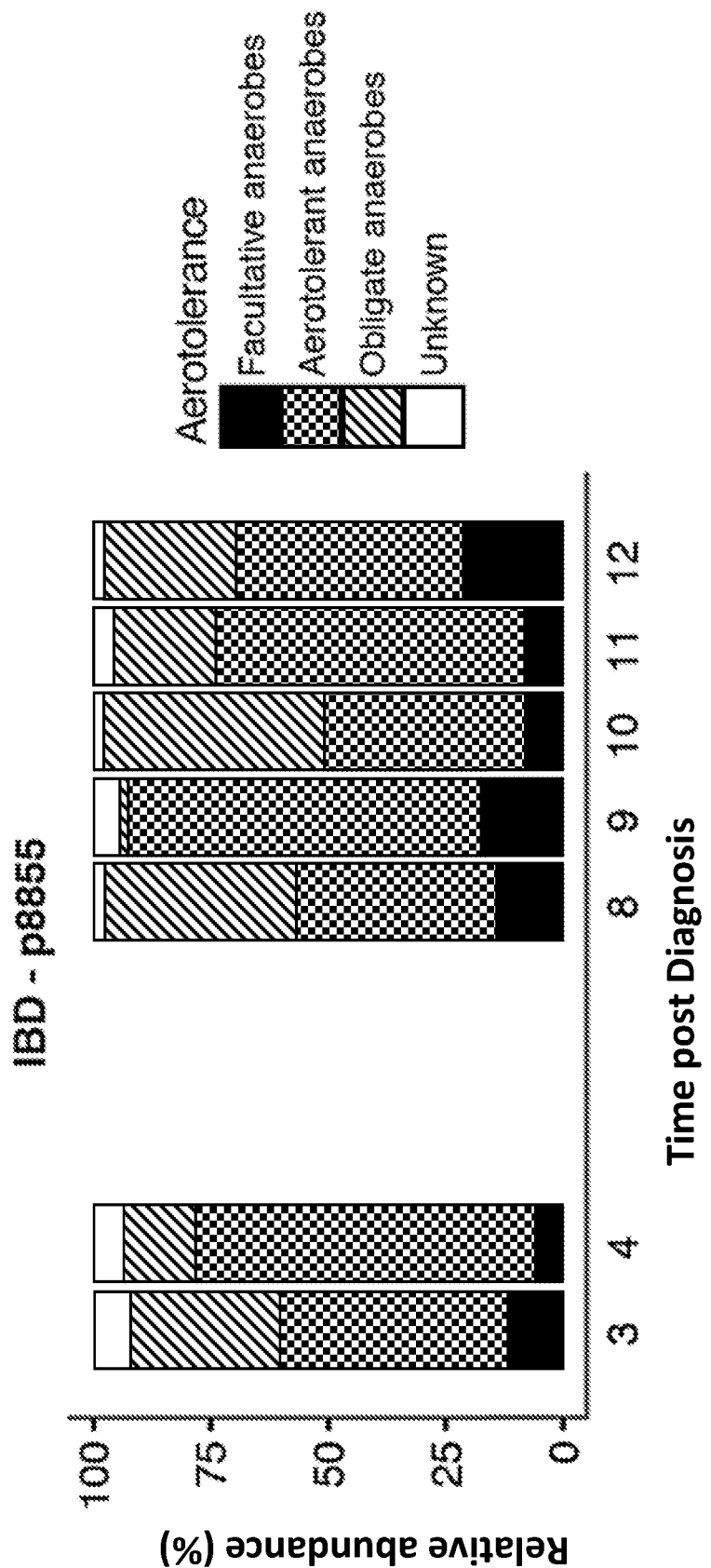
Figure 2G:
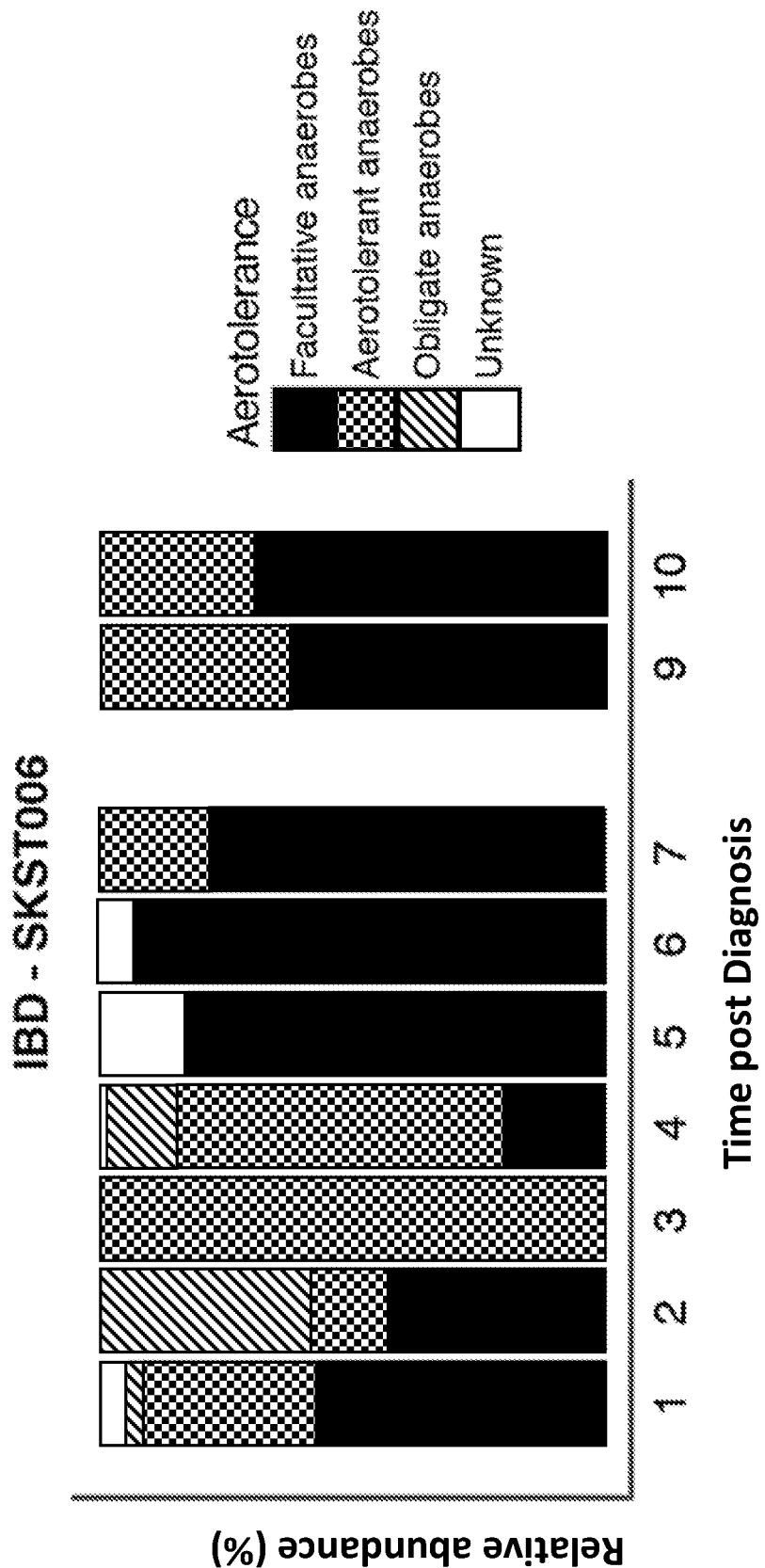
Figure 2H:
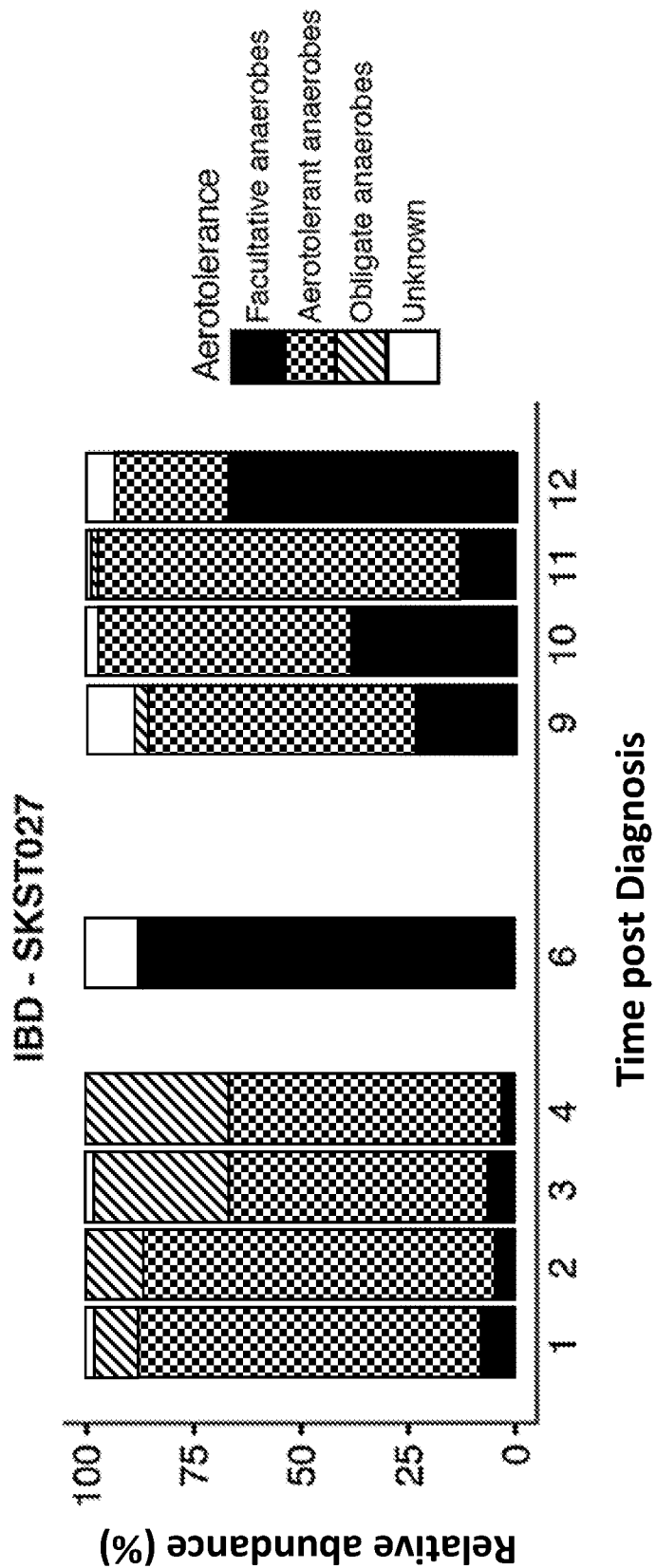

We found a consistent signal of increased abundance of facultative anaerobes across the LSS cohort as well as the Lewis et al. validation cohort (LSS nested anova+p-value=0.0478, validation cohort nested anova+p-value=0.005; FIG. 2A). The mean relative abundance of facultative anaerobes in controls from the HMP, LSS, and Lewis et al. validation cohort was 1.36, 1.78, and 1.45, respectively while the mean relative abundance of facultative anaerobes in individuals with IBD in LSS and Lewis et al. validation cohort was 9.73 and 19.48 respectively. Thus, a key commonality among many individuals with IBD is the increased abundance of facultative anaerobes, potentially to deal with the increased oxidative stress of the IBD gut.

Although facultative anaerobes are increased in general in IBD, individuals vary dramatically in which facultative anaerobes they carry. We identified 49 facultative anaerobes present at much higher abundance in IBD patients than in controls (at least one sample greater than 5% relative abundance) (Table 6). None of these species are typical high-abundance colonizers of the gut, and none of these species was present at greater than 5% abundance in any of the control samples, including stool samples from healthy individuals from the HMP. Many facultative anaerobe species only appeared at high abundance in a single sample. These 49 facultative anaerobes are taxonomically diverse with representatives from: Proteobacteria, Firmicutes, and Actinobacteria. The taxonomic diversity of the functionally redundant facultative anaerobes found to be increased in IBD suggests that the resistance to oxidative stress is a key factor shaping the composition of the gut microbiome in IBD.

TABLE 6

Facultative anaerobes found in greater than 5% relative abundance in at least one sample LSS and the Lewis et al. validation cohort. None of these species appears in greater than 5% abundance in any of the 80 HMP samples.

| Species | Cumulative IBD Abundance | # Samples >5% relab |
|---|---|---|
| Escherichia_coli | 1650.59981 | 68 |
| Haemophilus_parainfluenzae | 417.98925 | 25 |
| Streptococcus_salivarius | 470.87536 | 24 |
| Streptococcus_thermophilus | 463.09158 | 21 |
| Klebsiella_pneumoniae | 526.25057 | 18 |
| Lactobacillus_gasseri | 440.61045 | 12 |
| Streptococcus_parasanguinis | 396.1666 | 12 |
| Morganella_morganii | 127.56041 | 11 |
| Enterococcus_faecalis | 164.22735 | 6 |
| Enterobacter_cloacae | 169.79446 | 6 |
| Lactobacillus_acidophilus | 136.2803 | 5 |
| Pediococcus_acidilactici | 103.59771 | 5 |
| Oscillibacter_unclassified | 208.61286 | 5 |
| Proteus_mirabilis | 142.69412 | 5 |
| Lactococcus_lactis | 90.99656 | 5 |
| Klebsiella_oxytoca | 97.81016 | 4 |
| Lactobacillus_crispatus | 260.51224 | 3 |
| Lactobacillus_fermentum | 58.92875 | 3 |
| Lactobacillus_plantarum | 58.18199 | 3 |
| Streptococcus_lutetiensis | 37.43059 | 3 |
| Burkholderiales_bacterium_1_1_47 | 114.43127 | 3 |
| Actinomyces_graevenitzii | 16.85404 | 2 |
| Actinomyces_odontolyticus | 69.66944 | 2 |
| Rothia_mucilaginosa | 23.17704 | 2 |
| Enterococcus_faecium | 57.03406 | 2 |
| Enterococcus_gallinarum | 49.64019 | 2 |
| Lactobacillus_casei_paracasei | 51.12187 | 2 |
| Lactobacillus_ruminis | 66.75547 | 2 |
| Citrobacter_freundii | 50.87246 | 2 |
| Staphylococcus_epidermidis | 35.11369 | 2 |
| Actinomyces_sp_ph3 | 6.511 | 1 |
| Enterococcus_asini | 11.49459 | 1 |
| Enterococcus_raffinosus | 6.96614 | 1 |
| Lactobacillus_brevis | 17.43022 | 1 |
| Lactobacillus_mucosae | 10.44922 | 1 |
| Lactobacillus_rhamnosus | 25.22647 | 1 |
| Lactobacillus_salivarius | 26.09797 | 1 |
| Leuconostoc_unclassified | 13.18224 | 1 |
| Streptococcus_mitis_oralis_pneumoniae | 37.65145 | 1 |
| Erysipelotrichaceae_bacterium_5_2_54FAA | 16.50523 | 1 |
| Erysipelotrichaceae_bacterium_6_1_45 | 37.19088 | 1 |
| Eubacterium_biforme | 31.17557 | 1 |
| Eubacterium_dolichum | 18.19514 | 1 |
| Enterobacter_asburiae | 11.93924 | 1 |
| Klebsiella_sp_MS_92_3 | 33.3082 | 1 |
| Proteus_penneri | 6.89755 | 1 |
| Serratia_marcescens | 43.8974 | 1 |
| Aggregatibacter_segnis | 31.45823 | 1 |
| Staphylococcus_hominis | 65.5681 | 1 |

E. Transient Blooms of *Ruminococcus Gnavus* in IBD

*Ruminococcus gnavus* was a particularly unusual member of the aerotolerant subset of species in the preceding analysis that we decided to focus on.

Figure 3A:
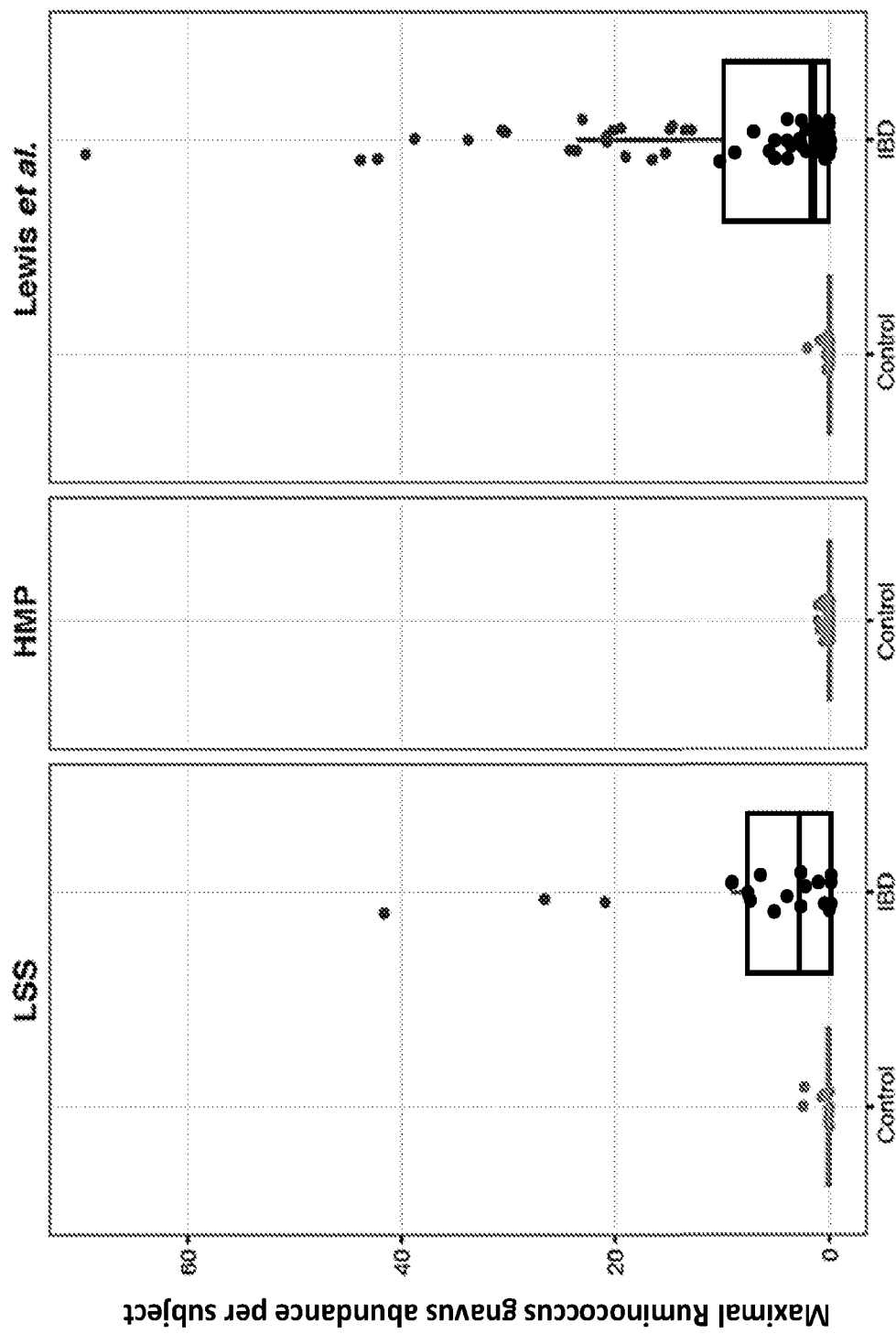
FIGS. 3A-C provide graphs showing that *R. gnavus* transiently dominates the gut microbiome in individuals with IBD. (A) Relative abundance of *R. gnavus* in healthy controls (HC) and inflammatory bowel disease (IBD) from the LSS and Lewis et al. validation cohorts. Lewis et al., Inflammation, Antibiotics, And Diet as Environmental Stressors of the Gut Microbiome in Pediatric Crohn's Disease, Cell Host Microbe 18(4):489-500 (2015). (B) The longitudinal relative abundance of *R. gnavus* in the LSS cohort from individuals with IBD. (C) The longitudinal relative abundance of *R. gnavus* from the Lewis et al. validation cohort.
Figure 3B:
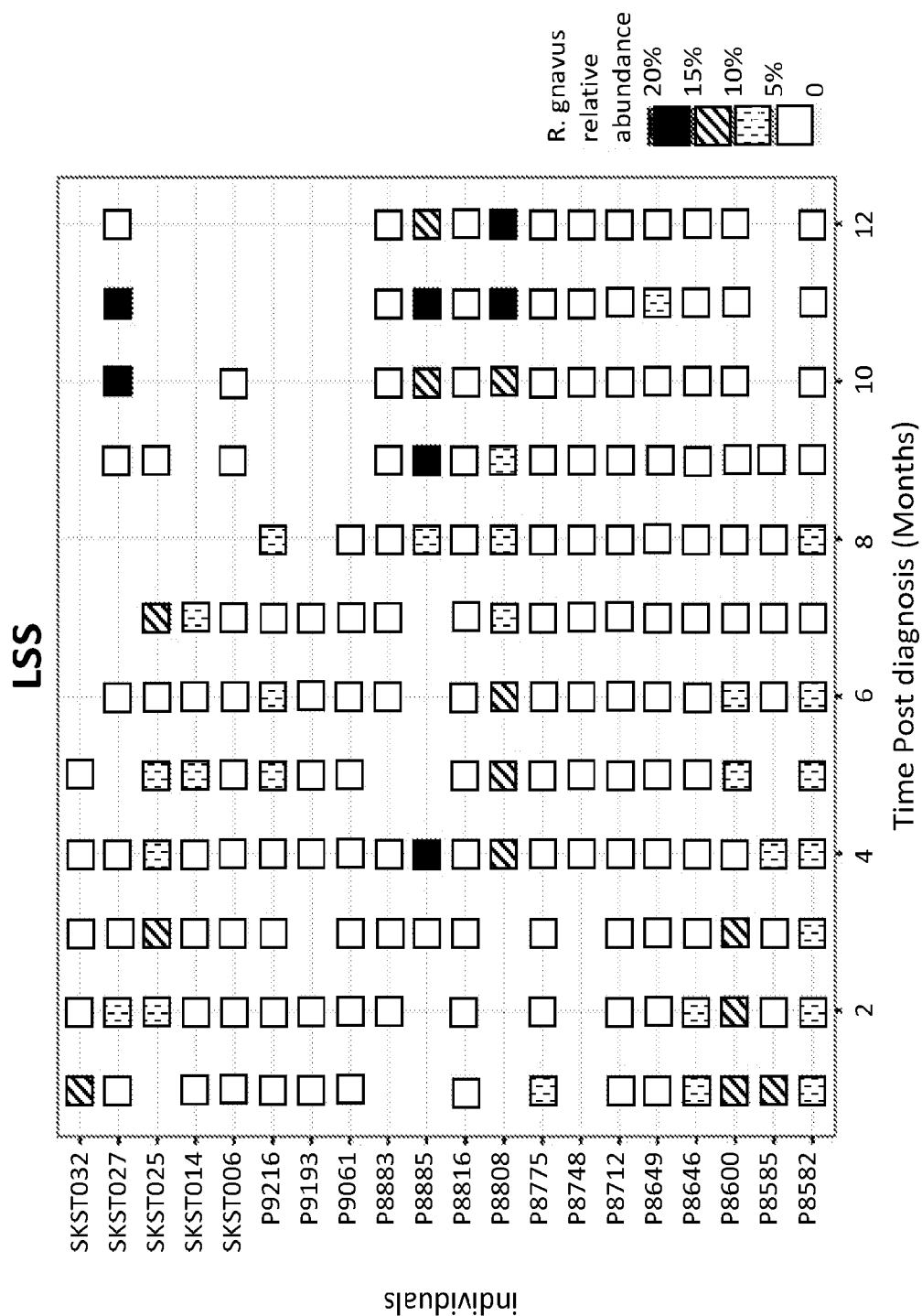
Figure 3C:
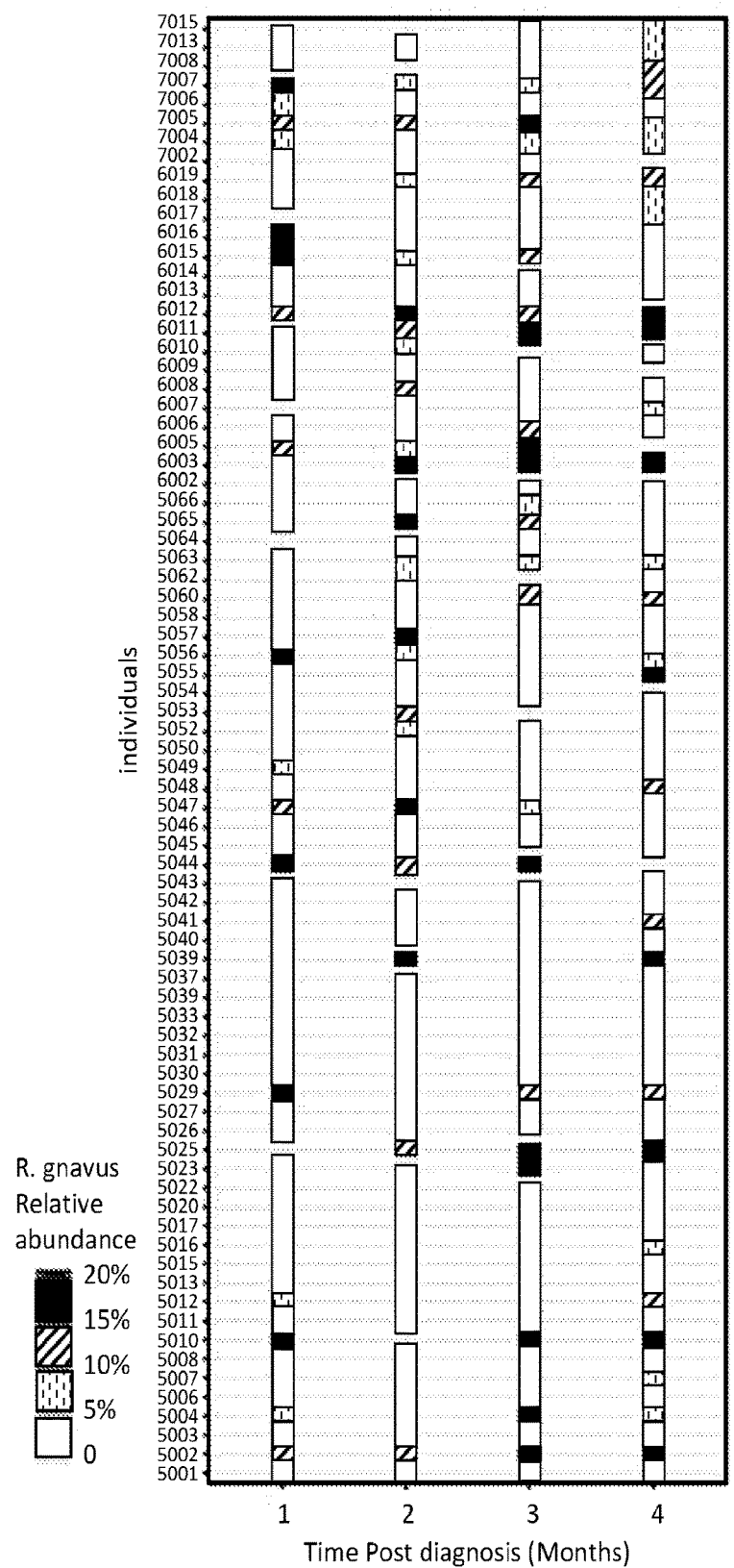
Figure 4:
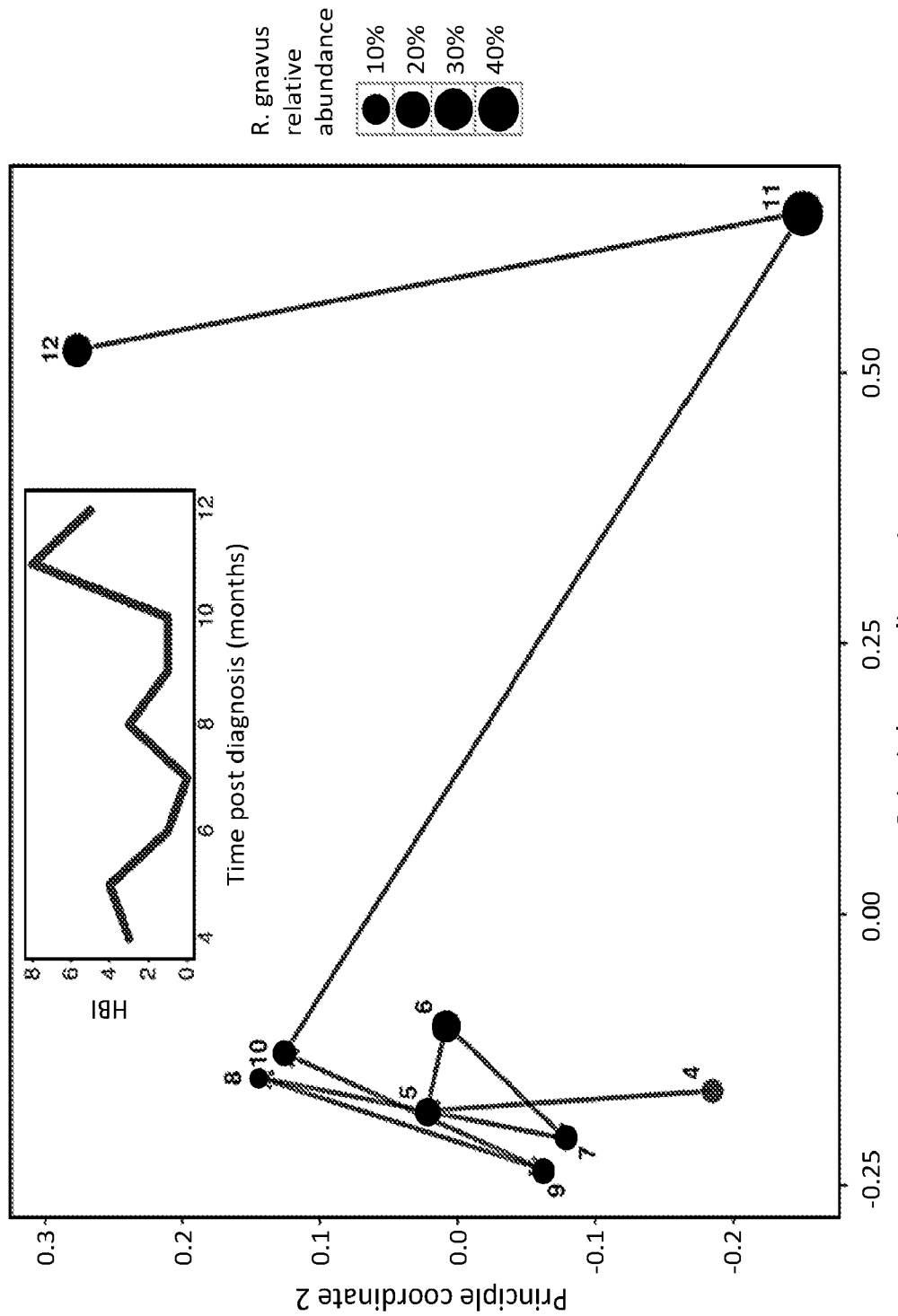
FIG. 4 shows a principle coordinates analysis (pCoA) of Bray-Curtis similarity of the species of individual p8808. Month 11 corresponds to the dramatic, transient increase of *R. gnavus* and clinical indications of inflammation (inset).

The abundance of *R. gnavus* was significantly increased in IBD compared to controls in the LSS (MaAsLin p=0.0265) and validation cohort (MaAsLin p=0.0098). In several individuals, a bloom of *R. gnavus* dominates the gut microbiome with a maximum relative abundance of 41.6% in the LSS cohort, and 69.5% in the replication cohort (FIG. 3). The maximum relative abundance in any controls was 2.44%. 20 samples from 8 individuals had elevated abundance of *R. gnavus* (here defined as relab>5%) as well as 53 samples from the replication cohort. To further explore the abundance of *R. gnavus* in healthy adults, we analyzed the stool metagenomic from healthy individuals from the HMP. The maximum relative abundance in the 80 samples was 1.06%. Individuals with IBD did not display permanent increased abundance of *R. gnavus*, but instead transient increases spanning only 1 or 2 time points (FIG. 3). (8/20 individuals have a transient increase in *R. gnavus*). The transient increases in *R. gnavus* often corresponded with clinical markers of inflammation. Elevated *R. gnavus* is specific to individuals with IBD in the LSS and validation cohorts. This example illustrates how the abundance pattern of *R. gnavus* confounds cross-sectional studies. Therefore, our longitudinal data was especially important to capture the massive but transient increases in the relative abundance of *R. gnavus*.

F. Strain-Level Analysis of Species in IBD

One of the unique advantages of metagenomic sequencing, over 16S for example, is the ability to examine microbial communities beyond the species level, and study strains when the coverage is sufficiently high. Understanding the strain-level dynamics is important, as in some cases it is a specific strain that is associated with the disease. For example, the adherent invasive *E. coli* (AIEC) strains, were specifically found to be enriched in IBD compared to health. Martinez-Medina and Garcia-Gil, *Escherichia coli* in Chronic Inflammatory Bowel Diseases: an Update on Adherent invasive *Escherichia coli* Pathogenicity, World Journal of Gastrointestinal Pathophysiology 5(3):213-227 (2014). To detect strain-level differences in our cohorts, we performed strain-level analysis with two tools: PanPhlAn and StrainPhlAn. PanPhlAn determines the presence or absence of all genes present in all available reference genomes for a species, hence allowing for the detection of functional differences encoded by the genomes of different strains. StrainPhlAn, on the other hand, uses SNPs in marker genes, which are specific to each species, to identify the dominant strain present for each species.

To compare strains between IBD patients and controls, we focused on species that are differentially abundant between IBD patients and healthy, yet have sufficient coverage in both sets of samples. Specifically, *E. coli, R. gnavus, F. prausnitzii* and *R. torques*. Similarly to healthy adults, strains found in IBD patients are generally maintained overtime. Franzosa et al., Identifying Personal Microbiomes Using Metagenomic Codes, Proc Natl Acad Sci USA E2930-E2938 (2015). However, we do identify differences between the functional potential found in IBD patients and controls. For example, for *E. coli*, which has previously shown to have IBD related strains (Martinez-Medina and Garcia-Gil, *Escherichia coli* in Chronic Inflammatory Bowel Diseases: an Update on Adherent invasive *Escherichia coli* Pathogenicity, World Journal of Gastrointestinal Pathophysiology 5(3):213-227 (2014)), we indeed found 132 IBD-specific genes, namely they are present in multiple IBD samples (with over 10× coverage across all samples), yet undetectable in all controls from both the LSS and validation cohorts including 80 stool metagenomes from the HMP (we call these IBD-specific genes). Of the 132 IBD-specific gene, the most-abundant one is a gene encoding a F17-like fimbrial adhesin protein that binds N-acetylglucosamine, an abundant glycan in the intestinal mucus layer. El Mazouari et al., F17-like Fimbriae from an Invasive *Escherichia coli* Strain Producing Cytotoxic Necrotizing Factor Type 2 Toxin, Infection and Immunity 62(6):2633-2638 (1994). This gene has been previously associated with pathogenic *E. coli*, potentially assisting in the adherence of the IBD-specific *E. coli* to the mucus layer, and possibly increasing its immunogenicity. Id. For *F. prausnitzii*, we identified four distinct strains, all present in both the IBD and controls.

Figure 6:
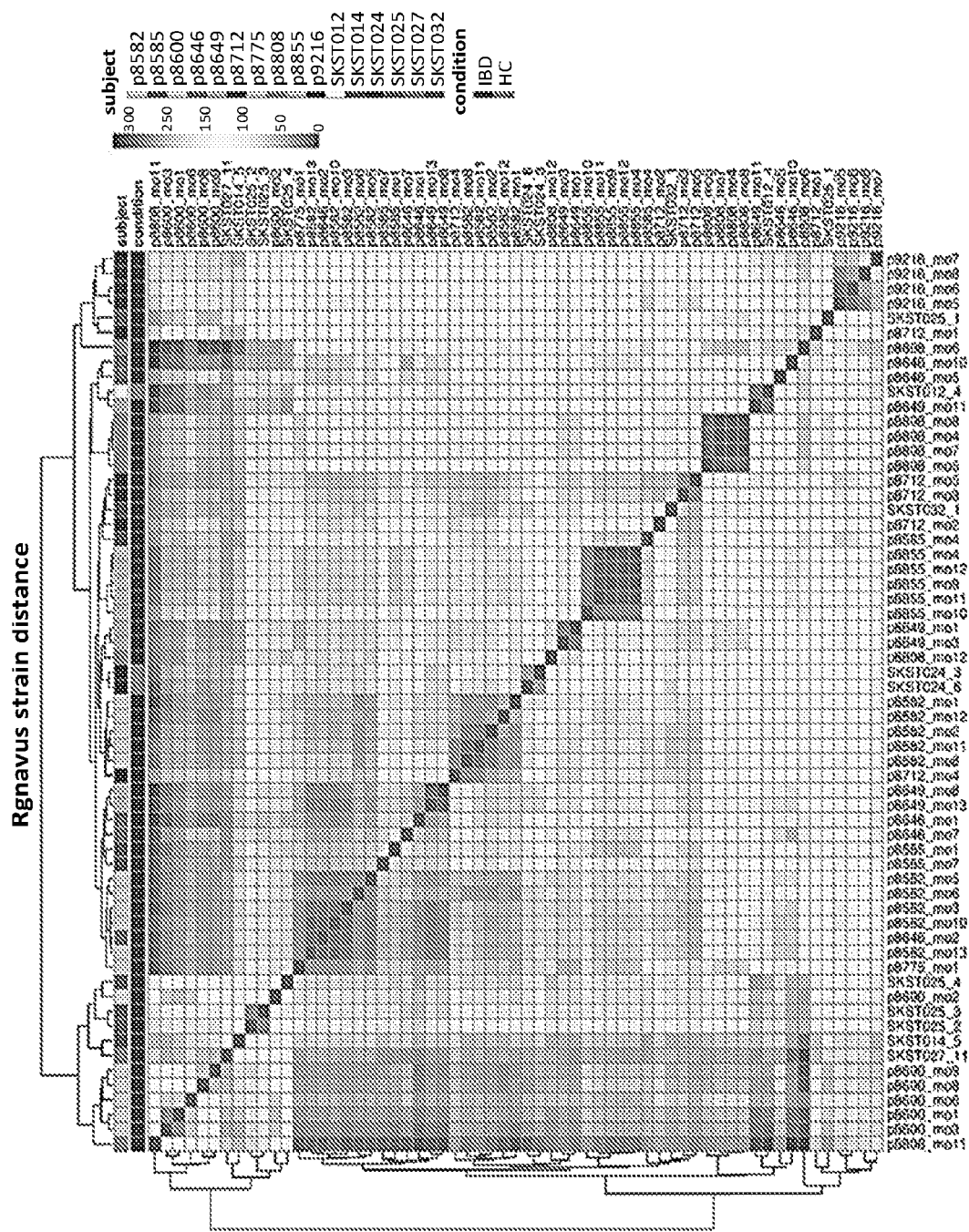
FIG. 6 shows a heatmap of *R. gnavus* SNP similarity from StrainPhlAn. Note that subject P8808 month 11 coincides with a massive increase in the relative abundance of *R. gnavus* and clinical signs of inflammation and it does not cluster with other P8808 samples.

Interestingly, in the case of *R. gnavus*, both PanPhlAn and StrainPhlAn identified two distinct groups. One group was present in both IBD and healthy subjects which we called *R. gnavus* group general. The second group was present only in individuals with IBD which we called the *R. gnavus* group IBD (FIG. 6). The available reference genomes for *R. gnavus* were from *R. gnavus* group General. Therefore, to obtain a reference genome from a *R. gnavus* group IBD, we performed a metagenomic assembly on a sample, p8808_mo11, that was predominately *R. gnavus* group IBD.

With the addition of the *R. gnavus* group IBD genome, we searched for IBD-specific genes in *R. gnavus* Unlike in the case of *F. prausnitzii* or *R. torques*, which had only five and one IBD-specific genes, respectively, we identified 142 *R. gnavus* IBD-specific genes. Due to this unique finding of such a large set of IBD-specific genes, we further investigated these two strains.

G. IBD-Specific Gene Clusters in *R. Gnavus*

We found that many *R. gnavus* IBD-specific genes are organized into four distinct genomic clusters (Table 7), strongly supporting our classification of these genes as differential. We identified four such distinct clusters. We next turned to study the functionality encoded by the each of these four clusters.

TABLE 7

Gene clusters specific to IBD from *R. gnavus* PanPhlAn

| Gene name | Sum IBD Coverage | Sum Healthy Coverage | Annotation |
| --- | --- | --- | --- |
| Cluster 1 | | | |
| G007090 | 362.63 | 0.14 | glycine betaine transport |
| g007091 | 236.406 | 0 | glycine betaine transport |
| g007092 | 392.573 | 0.336 | glycine betaine transport |
| g007093 | 383.696 | 7.536 | GNAT family N-acetyltransferase |
| G007094 | 291.148 | 0 | GntR transcriptional regulator |
| G007095 (10) | 170.716 | 0 | Internalin-J, LPXTG motif |
| Cluster 2 | 7 | | |
| g006853 | 253.939 | 0 | glycine betaine transport |
| g006854 | 122.838 | 0 | |
| Cluster 3 | 6-10 | | |
| g001652 | 115.31 | 0 | Collagen binding protein, LPXTG motif |
| g001653 | 107.729 | 0 | |
| g001654 | 120.99 | 0 | VWA domain protein |
| g001655 | 107.729 | 0 | |
| g001656 | 102.604 | 0 | |
| g001657 | 123.734 | 0 | |
| g001658 | 100.767 | 0 | |
| Cluster 4 | 4-6 | | |
| g005306 | 37.529 | 0 | LacI family transcriptional regulator |
| g005307 | 34.096 | 0 | sucrose 6 phosphate hydrolase GH32 |
| g005308 | 34.602 | 0.14 | sugar ABC transporter |
| g005309 | 36.827 | 0 | sugar permease |
| g005310 | 29.306 | 0 | sugar permease |
| g005311 | 1714.218 | 114.256 | GH18 |
| g005312 | 18.303 | 0 | hypothetical protein |
| g005313 | 25.75 | 0 | ABC transporter permease |

Genes in Cluster 1 include three glycine/betaine ABC transporters, an GNTR family transcriptional regulator, and an LPXTG motif containing protein. Glycine/betaine can confer increased tolerance to environmental stressors, such as osmotic stress and potentially oxidative stress. Liu et al., Glycine Betaine Improves Oxidative Stress Tolerance and Biocontrol Efficacy of the Antagonistic Yeast *Cystofillobasidium informominiatum*, International Journal of Food Microbiology 146(1):76-83 (2011). The ability to respond to stress, be it osmotic or oxidative, may be beneficial to colonize the IBD gut.

GNTR family transcriptional regulators are involved in the regulation of many genes, and therefore the presence of this gene in the IBD-specific strain could have far-reaching transcriptional consequences. Suvorova et al., GntR Family of Bacterial Transcription Factors and Their DNA Binding Motifs: Structure, Positioning and Co-Evolution, PLOS One 10(7):e0132618 (2015). With regards to the LPXTG motif proteins, gram-positive bacteria use the sortase pathway to synthesize pilli, which recognizes the LPXTG motif. Imam et al., Identification of Surprisingly Diverse Type IV Pili, Across a Broad Range of Gram-Positive Bacteria, PLOS One 6(12):e28919 (2011). Therefore, this gene may be involved in pilus biosynthesis, or at least a surface protein. LPXTG motif containing proteins are involved in virulence and colonization in many pathogens. Sabet et al., LPXTG Protein InlJ, a Newly Identified Internalin Involved in *Listeria monocytogenes* Virulence, Infection and Immunity 73(10):6912-6922 (2005). In fact, the closest KEGG gene to this LPXTG motif containing gene was an Internalin J, a *Listeria monocytogenes* invasion factor (e-value=$2\times10^{-7}$). Id Therefore, this duster of IBD-specific genes may help adhere to the epithelia, which may provoke an immune response.

Cluster 2 is present in 7 individuals with IBD and contains an additional glycine/betaine ABC transporter. Interestingly, in the six sequenced *R. gnavus* reference genomes, there is only a single annotated glycine/betaine ABC transporter, which is distinct from the four described here (three in Cluster 1 and one in Cluster 2). Therefore, this IBD-specific strain expanded the number of glycine/betaine ABC transporters, potentially enabling a better colonization of the IBD gut.

Cluster 3 contains seven neighboring genes which are present only at samples from IBD patients. Two of these genes are annotated as involved in adhesion (a collagen binding protein, and a VWA domain protein (Whittaker and Hynes, Distribution and Evolution of von Willebrand/Integrin A Domains: Widely Dispersed Domains with Roles in Cell Adhesion and Elsewhere, Molecular Biology of the cell 13:3369-3387 (2002)), while the rest are annotated as "hypothetical proteins". Adhesion to the collagen in the host epithelia may help *R. gnavus* reside within the mucus layer, which may be its primary food source. In fact, it was recently noted that *Akkermansia muciniphila*, a prolific mucogenic species in healthy individuals, binds to the host epithelia instead of to mucus itself. Reunanen et al., *Akkermansia muciniphila* Adheres to Enterocytes and Strengthens the Integrity of the Epithelial Cell Layer, Applied and Environmental Microbiology 81(11):3655-3662 (2015).

Cluster 4 has genes for sugar catabolism, including a LacI transcriptional regulator, glycoside hydrolases, and sugar ABC transporters. One of the glycoside hydrolases belongs to the GH18 family, and possibly encodes an endo-β-N-acetylglucosaminidases, a constituent component of the mucus layer, which would be beneficial to digest mucosal glycans.

H. Longitudinal Strain Dynamics of R. Gnaws in IBD

Figure 5:
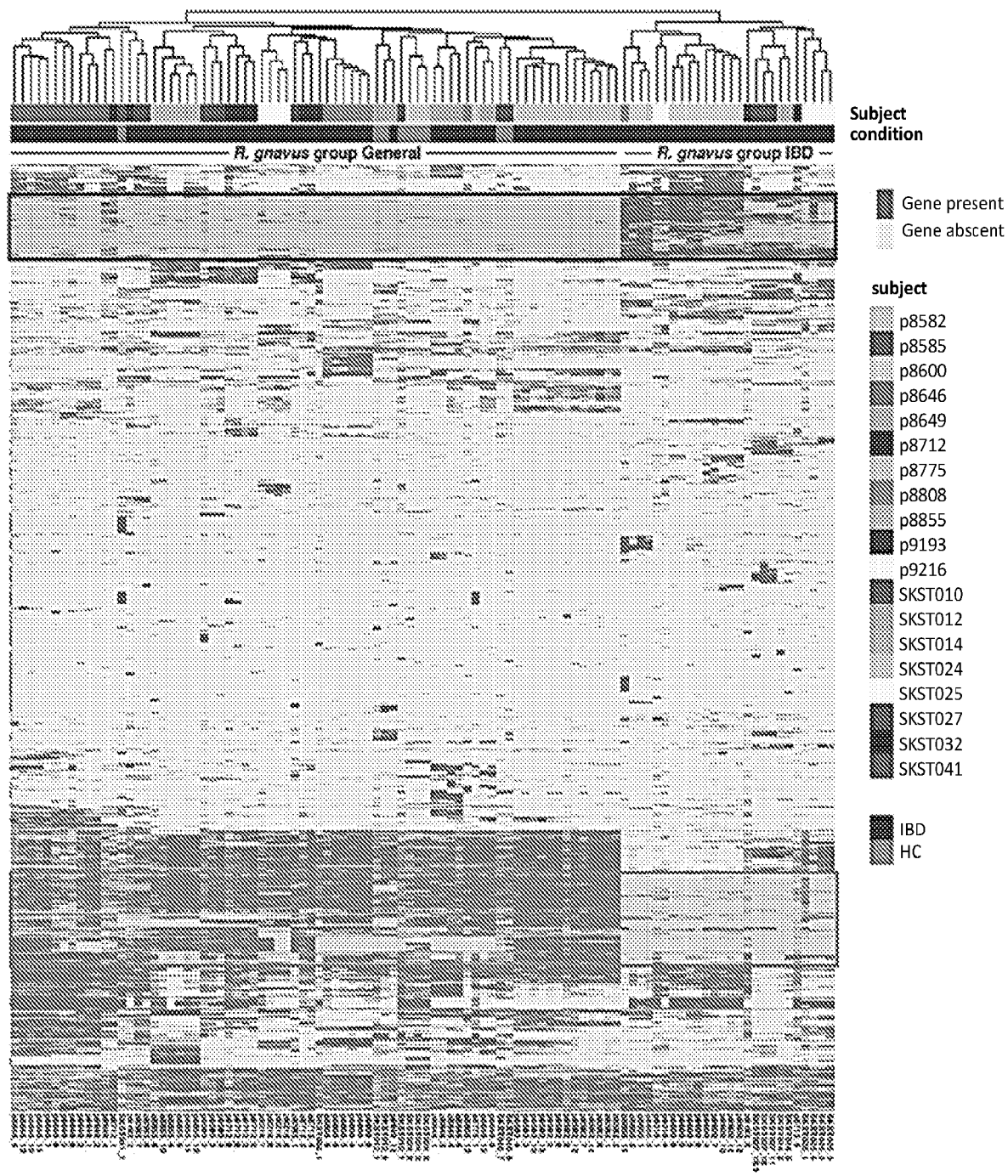
FIG. 5 provides the results of a pangenome analysis of *R. gnavus* using PanPhlAn showing the presence or absence of every gene in the *R. gnavus* pangenome. Clustering the results reveal two groups of *R. gnavus*, the *R. gnavus* group General and *R. gnavus* group IBD, which is present only in individuals with IBD. The upper transparent rectangle contains genes enriched in *R. gnavus* group IBD. The lower transparent rectangle contains genes many genes missing from *R. gnavus* group IBD.

The difference between *R. gnavus* group General and *R. gnavus* group IBD may have functional consequences in vivo as well, as exemplified by patient 8808 (FIG. 5, YYE). We have 9 samples from this subject, spanning from months 4 to 12 post-diagnosis. The gut microbiome of this individual undergoes a drastic shift between months 10 and 11, which coincides with an increase in the Harvey-Bradshaw Index (HBI), and fecal calprotectin indicating increased inflammation. During this time, this community lost many obligate anaerobes species (including *Faecalibacterium prausnitzii, Roseburia species, Eubacterium* species, and *Eggerthella* species), and has become entirely dominated by aerotolerant or facultatively anaerobic species (including *R. gnavus* (41.6%), *E. coli* (9.4%), *Clostridium nexile* (9.6%), and *B. producta* (4.3%)). In the following month, the relative abundance of *R. gnavus* decreases to 14.9%, and obligate anaerobes start to return. The higher abundance of *R. gnavus* found at month 11 is not merely an expansion of the previous strain, but rather a bloom of the IBD-specific group of *R. gnavus*. An additional three individuals (9216, 8712, and 9193) have blooms of the IBD-specific group of *R. gnavus* during the observation period (FIG. 5, YYE). Three individuals only have the IBD-specific group of *R. gnavus* (SKST014, SKST025, and SKST027), all of which did not respond to treatment (FIG. 5, YYE). Together, these results suggest that the *R. gnavus* group IBD has a distinct functional repertoire, potentially allowing for enhanced colonization of the specific environment of the inflamed gut.

I. Metabolic Niche of *R. Gnavus*

Next, we wanted to understand what is the biogeographic compartment in which *R. gnavus* resides within the gut Members from the *Blautia* genus are enriched in colon (Reunanen et al., *Akkermansia muciniphila* Adheres to Enterocytes and Strengthens the Integrity of the Epithelial Cell Layer, Applied and Environmental Microbiology 81(11):3655-3662 (2015)), and we wanted to ask whether *R. gnavus* is mucogenic, namely, capable of utilizing the glycans in the mucus layer as a source of energy, or is it utilizing energy sources found in the gut lumen (either glycans or not). The utilization of these distinct energy sources would require distinct functional capabilities.

First, we can examine whether *R. gnavus* utilizes non-glycans as an energy source, like other members of its genus. For example, *Blautia hydrogenotrophica* and *Blautia producta*, are acetogens, which can convert carbon dioxide and molecular hydrogen, found in the gut lumen, into acetate using the Wood-Ljungdahl pathway. Rey et al., Dissecting the in Vivo Metabolic Potential of Two Human Gut Acetogens, The Journal of Biological Chemistry 285(29):22082-22090 (2010). To determine whether *R. gnavus* is also an acetogen, we annotated the Wood-Ljungdahl pathway using homologous genes from *B. hydrogenotrophica*. Id We found that the Wood-Ljungdahl pathway in *R. gnavus* is missing the crucial gene Acetyl-CoA synthetase as well as the corrinoid iron-sulfur small subunit (Table 8), suggesting this pathway is non-functional in *R. gnavus*, and must use a different pathway for energy production.

TABLE 8

Annotation of acetogenesis pathways in other gut bacteria

| Function | *Blautia hydrogenotrophica* | | *Ruinococcus gnavus* ATCC 24149 | | *Blautia producta* ATCC 27340 | |
| --- | --- | --- | --- | --- | --- | --- |
| Formate dehydrogenase (alpha) | RUMHYD_00602 | 0.0 | EDN76601.1 | 6.00E−25 | WP_018596374.1 | 0.00E+00 |
| Formate dehydrogenase (beta) | RUMHYD_03629 | 2.00E−67 | EDN78250.1, EDN79049.1 | 0 | WP_018593852.1 | 0.00E+00 |
| Formyltetrahydrofolate synthetase | RUMHYD_03927 | 0.0 | EDN79055.1 | 0 | WP_018593053.1 | 0.00E+00 |
| Formyltetrahydrofolate cyclohydrolase | RUMHYD_00325 | 1E−63 | EDN79054.1 | 4.00E−65 | WP_018597559.1 | 0.00E+00 |
| methylenetetrahydrofolate dehydrogenase | RUMHYD_00325 | 1E−63 | EDN79508.1 | 2.00E−36 | WP_018597559.1 | 0.00E+00 |
| methylenetetrahydrofolate reductase | RUMHYD_01189 | 1E−56 | EDN79284.1 | 0.009 | WP_018597547.1 | 2.00E−12 |
| Methyltransferase | RUMHYD_00321 | 1E−31 | EDN79286.1 | 3.00E−24 | WP_018597554.1 | 1.00E−157 |
| Carbon monoxide dehydrogenase alpha | RUMHYD_03382 | 1E−122 | EDN77790.1 | 3.00E−55 | WP_018597549.1 | 0.00E+00 |
| Carbon monoxide dehydrogenase beta | RUMHYD_00315 | | absent | | WP_018598141.1, WP_018597958.1 | 3.00E−94 |
| Corrinoid (small subunit) | RUMHYD_00319 | 4E−41 | absent | | WP_018597552.1 | 6.00E−147 |
| Corrinoid (large subunit) | RUMHYD_00320- RUMHYD_00321 | 3E−55 | EDN79286.1 | 3.00E−24 | WP_018597553.1, WP_018597554.1 | 1.00E−171 |
| Acetyl-CoA synthetase | RUMHYD_03381/ RUMHYD_00318/ RUMHYD_00317 | 1E−171 | absent | | WP_018597551.1 | 0.00E+00 |
| P-transacetylase | RUMHYD_00259/ RUMHYD_00555/ RUMHYD_01109 | NA | EDN76817.1 | 0 | WP_018594744.1 | 9.00E−65 |
| Acetate Kinase | RUMHYD_00260 | 1.00E−124 | EDN76816.1 | 1.00E−171 | WP_026255683.1 | 0.00E+00 |

TABLE 8-continued

Annotation of acetogenesis pathways in other gut bacteria

| Function | Ruminococcus torques ATCC 27756 | | Blautia obeum ATCC 29147 | | Blautia hansenii DSM 20538 | |
|---|---|---|---|---|---|---|
| Formate dehydrogenase (alpha) | WP_009242294.1 | 7.00E−31 | WP_005423490.1 | 1.00E−34 | WP_009246297.1 | 4.00E−36 |
| Formate dehydrogenase (beta) | WP_004847808.1 | 2.00E−66 | WP_005426829.1 | 0 | WP_003020910.1 | 0 |
| Formyltetrahydrofolate synthetase | WP_004847802.1 | 0.00E+00 | WP_005424269.1 | 0 | absent | |
| Formyltetrahydrofolate cyclohydrolase | WP_004847804.1 | 1.00E−68 | WP_005423502.1 | 0 | WP_003021444.1 | 0 |
| methylenetetrahydrofolate dehydrogenase | WP_004847804.1 | 1.00E−68 | WP_005423502.1 | 0 | WP_003021444.1 | 0 |
| methylenetetrahydrofolate reductase | absent | | WP_005428196.1 | 0 | absent | |
| Methyltransferase | WP_004844944.1 | 4.00E−26 | WP_005425370.1 | 0 | WP_003021416.1 | 3.00E−157 |
| Carbon monoxide dehydrogenase alpha | WP_004845398.1 | 3.00E−82 | WP_005425377.1 | 0 | WP_003021398.1 | 0 |
| Carbon monoxide dehydrogenase beta | absent | | absent | | WP_004222259.1 | 7.00E−77 |
| Corrinoid (small subunit) | absent | | WP_005425373.1 | 1.00E−150 | WP_003021408.1 | 2.00E−143 |
| Corrinoid (large subunit) | absent | | WP_005425371.1 | 0 | WP_003021413.1 | 2.00E−176 |
| Acetyl-CoA synthetase | absent | | WP_005425374.1, WP_044925744.1 | 0 | WP_003021404.1 | 0.00E+00 |
| P-transacetylase | WP_004846207.1 | 0.00E+00 | WP_022389420.1 | 0 | absent | |
| Acetate Kinase | WP_004846206.1 | 1.00E−171 | WP_005425411.1 | 4.00E−171 | WP.003021213.1 | 0.00E+00 |

Next, we wanted to understand whether *R. gnavus* is capable of utilizing glycans found in the mucus layer. Previous studies have shown an increased abundance of *R. gnavus* in the mucus of IBD patients, and hypothesized that *R. gnavus* may be mucogenic (Png et al. 2010) (PMID 20648002). Furthermore, certain strains of *R. gnavus* were experimentally shown to digest mucus. Crost et al., Utilization of Mucin Glycans by the Human Gut Symbiont *Ruminococcus gnavus* is Strain-Dependent, PLOS One 8(10):e76341 (2013); Crost et al., The Mucin-degradation Strategy of *Ruminococcus gnavus*. The Importance of Intramolecular Trans-sialidases, Gut Microbes 7(4):302-312 (2016). The pangenome of *R. gnavus* includes glycoside hydrolases families (GH29, GH95, and GH33) necessary to cleave terminal fucose and sialic acid residues from mucus. Crost et al. (2013); Crost et al. (2016). Interestingly, *R. gnavus* also has a unique function of cleaving and modifying sialic acids which can be used exclusively by *R. gnavus* through the GH33 trans-sialidase Crost et al. 2016; Tailford et al., Discovery of Intramolecular Trans-sialidases in Human Gut Microbiota Suggests Novel Mechanisms of Mucosal Adaptation, Nature Communications 6:7642 (2015). We wanted to determine whether the *R. gnavus* in our samples possessed the key genes required for mucus utilization. In our pangenome analysis, we detected the presence of 6 of these glycoside hydrolases in 20 out of 20 individuals and 12 in at least 17 individuals (Table 9). Thus, we concluded that the strains of *R. gnavus* present in the IBD gut likely occupy a mucogenic niche. Occupying this niche increases the opportunity to elicit inflammation, merely by being in close proximity to the host epithelia.

TABLE 9

Pangenome analysis of *R. gnavus* glycoside hydrolases involved in mucus utilization. *R. gnavus* was detected in 20 of 20 individuals. CAZY annotations were retrieved from ProGenomes (Mende 2017) (PMC 5210662)

| CAZY Classification | PanPhlAn identifier | Present in individuals |
|---|---|---|
| GH29 | g000635 | 0 |
| GH95 | g000676 | 5 |
| GH29 | g001562 | 0 |
| GH29 | g001578 | 19 |
| GH95 | g001597 | 6 |
| GH95 | g002881 | 20 |
| GH95 | g002982 | 18 |
| GH29 | g003046 | 17 |
| GH95 | g003139 | 20 |
| GH95 | g003144 | 19 |
| GH33 | g003577 | 11 |
| GH95 | g003631 | 20 |
| GH33 | g004607 | 17 |
| GH95 | g005357 | 19 |
| GH95 | g006085 | 20 |
| GH29 | g006118 | 20 |
| GH95 | g007627 | 20 |
| GH29 | g000635 | 0 |

Example 3: Discussion

The results presented here confirm that a major feature of the dysbiosis of the gut microbiome in IBD is a shift towards facultative anaerobes and away from obligate anaerobes. Importantly, resistance to oxidative stress is a polyphyletic trait, and is not well addressed by taxonomic binning. This shift has several important implications for the physiology of the gut in IBD. The obligate anaerobes that are often depleted in IBD are the major butyrate-producing species in the gut, many of which have anti-inflammatory effects.

Lewis et al., Inflammation, Antibiotics, and Diet as Environmental Stressors of the Gut Microbiome in Pediatric Crohn's Disease, Cell Host Microbe 18(4):486-500, doi: 10.1016/j.chom.2015.09.008 (2015). Many of the species with increased abundance in IBD are not typical colonizers of the gut microbiome, but are more common in other sites like the mouth or skin. The species may not be adapted to promote intestinal homeostasis in the way that many native gut colonizers are, which could promote inflammation. Additionally, the increased abundance of fungal species, which are facultative anaerobes, reported in by Lewis et al. could also be explained by the increased oxidative stress of the IBD gut. Id.

The WMS sequencing used here allowed for increased resolution of taxonomic profiling, which revealed that *R. gnavus* transiently dominates the microbiome of patients with IBD. This signal of high *R. gnavus* was specific to patients with IBD which may be beneficial in future efforts to diagnose IBD from stool microbiome sequencing. We then increased the resolution further by performing state-of-the-art strain-level and pangenome analysis allowing for the identification of a *R. gnavus* strain specific to individuals with IBD. The data show that is likely an important member of the dysbiotic consortium in IBD because it is resistant to oxidative stress, likely mucogenic, and this behavior is likely enhanced by IBD-strain-specific genes involved in adhesion, and response to stress.

Whether the increased abundance of *R. gnavus* in IBD is a cause or effect of inflammation is currently unknown. At the very least, *R. gnavus* is a superlative colonizer of the inflamed IBD gut. However, it is also possible that *R. gnavus* contributes to or exacerbates the excessive immune response to the gut microbiome in IBD. *R. gnavus* has notable similarities to *E. coli*, which has been implicated as a potential provocative agent in IBD. Both the abundance of *E. coli* and *R. gnavus* have increased relative abundances in IBD. In the case of *E. coli*, defects in NOD2, a major risk allele for IBD, have been associated with increased abundance of Enterobactericeae, the family containing *E. coli*.

Similarly, the abundance of *R. gnavus* is kept in check by the innate immune system. For example, in SEl1L deficient mice, which lack normal Paneth cell function, the abundance of *R. gnavus* increases 10 fold. Sun et al., Epithelial Sel1L is Required for the Maintenance of Intestinal Homeostasis, Molecular Biology of the Cell 27:483-490 (2016). Paneth cell defects are observed in IBD patients, and the level of Paneth cell a-defensins is decreased in IBD which could lead increases in the relative abundance of *R. gnavus* like observed in SEl1L deficient mice. Simms et al., Reduced α-defensin Expression is Associated with Inflammation and Not NOD2 Mutation Status in Ileal Crohn's Disease, Gut 57(7):903-910 (2008).

Increased intestinal permeability has been implicated in the pathogenesis of IBD and T1D. Michielan and D'Inca, Intestinal Permeability in Inflammatory Bowel Disease: Pathogenesis, Clinical Evaluation, and Therapy of Leaky Gut, Mediators of Inflammation 2015:628157 (2015); Vaarala et al., The "Perfect Storm" for Type 1 Diabetes: the Complex Interplay Between Intestinal Microbiota, Gut Permeability, and Mucosal Immunity, Diabetes 57(10):2555-2562 (2008). The protective mucus layer is thinner in IBD. Strugala et al., Thickness and Continuity of the Adherent Colonic Mucus Barrier in Active and Quiescent Ulcerative Colitis and Crohn's Disease, International Journal of Clinical Practice 62:762-769 (2008). The mucolytic activity of *R. gnavus* could contribute to increased intestinal permeability observed in these diseases.

Both *E. coli* and *R. gnavus* live in close proximity to the colonic epithelia and immune system. Adherent, invasive *E. coli* encode genes that allow for adherence host cells, which can trigger inflammation. As it likely occupies a mucogenic niche, *R. gnavus* must also be closely associated with the host epithelia because the mucus layer in the colon is only approximately 10-80 microns thick. Id Our pangenome and comparative genomic analysis identified genes potentially involved in adhesion specific to IBD which may allow for enhanced adhesion to the host epithelia. Therefore, the overabundance of *R. gnavus* in IBD could elicit inflammation. Future studies should experimentally address the implications of the large increases of *R. gnavus* in IBD.

Ideally, biopsy samples could be sequenced with WMS to determine which species are present in the mucus vs. lumen of IBD patients. However, WMS is currently not cost-effective on biopsy samples because almost all DNA present in biopsies is human-derived.

Example 4: *Ruminococcus gnavus* clades differ by CRISPR genes

Figure 7A:
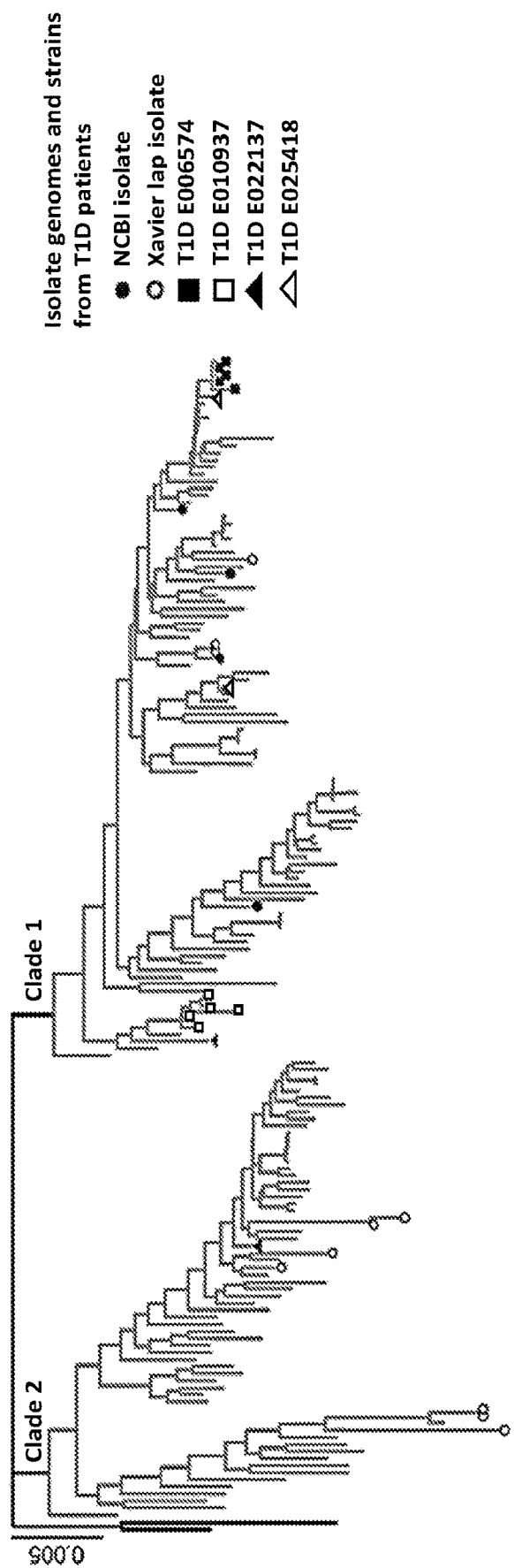
FIGS. 7A-B show *R. gnavus* clades in infant gut.

Increased abundance of *Ruminococcus gnavus* has been implicated in IBD and T1D onset. Our SNP haplotype- and pangenome-based strain analyses revealed that *R. gnavus* strains have a bimodal similarity distribution, implicative of two distinct clades or subspecies. Phylogenetic analysis of the SNP haplotypes revealed two distinct subspecies clades as previously described in adult IBD patients (FIG. 7A). Within the DIABIMMUNE cohort, 39 non-IBD infants harbored a strain belonging to the Glade highlighted in FIG. 7A (Glade 2), which has been previously found only in adults with IBD. Anecdotally, the other Glade (Glade 1) that was present in the majority (92/152) of the DIABIMMUNE samples was also found in 15 samples from 4 children with clinical T1D diagnosis, whereas lade 2 was present in only one sample from a T1D-positive child who harbored Glade 1 in separate samples.

Figure 7B:
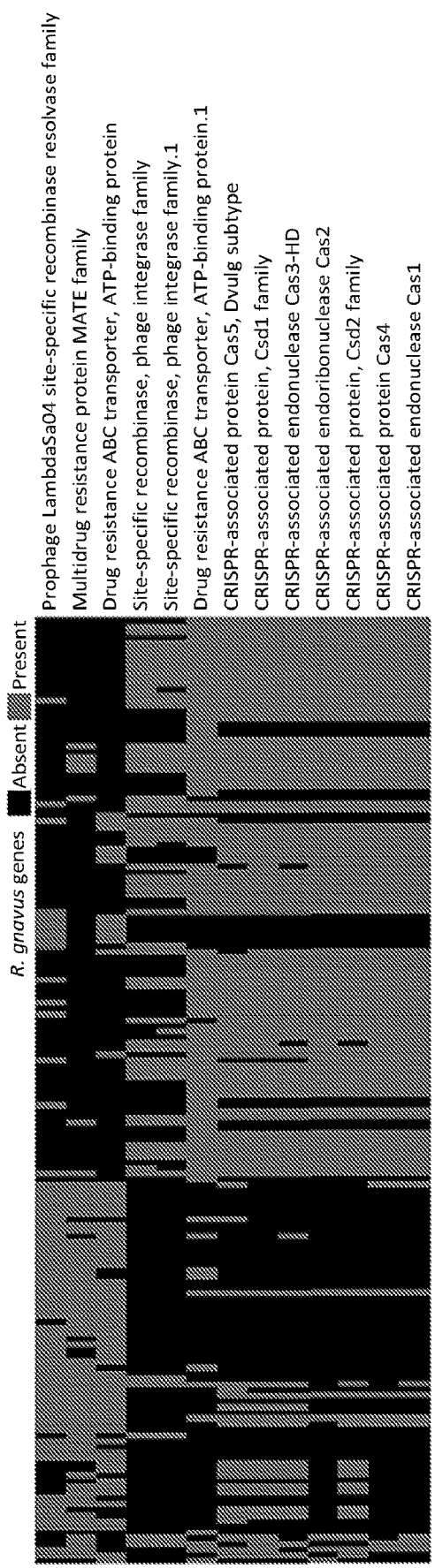

To survey any functional differences between these two *R. gnavus* clades, we compared the prevalence of each gene in an extended *R. gnavus* pangenome between the clades (data not shown). Among the genes with differential prevalences across the clades, we found multiple genes involved in the CRISPR system, phage activity, and drug resistance (FIG. 7B), providing speculative explanations for how these clades may have diverged. For example, the CRISPR system provides a bacterial defense mechanism against phages; adaptation might occur in one lade under conditions abundant with *R. gnavus*-targeting phages, while the other lade might lose CRISPR genes in the absence of similar pressure.

Example 5: Certain Embodiments

The following numbered items provide additional support for and descriptions of the embodiments herein.

Item 1. A method of treating IBD in a human subject comprising administering an effective amount of at least one antimicrobial agent effective for eliminating or suppressing *R. gnavus*.

Item 2. A method of treating IBD in a human subject comprising administering an effective amount of at least one IBD therapy to a subject having a gut microbiome comprising *R. gnavus*.

Item 3 A method of diagnosing IBD in a human subject comprising
  a. determining from a gut microbiome sample whether the gut microbiome comprises *R. gnavus* and b. diagnosing the subject as having IBD when *R. gnavus* is identified.

Item 4. The method of any one of items 1-3, wherein the IBD is Crohn's disease or ulcerative colitis.

Item 5. The method of any one of items 1-3, wherein the IBD is collagenous colitis, lymphocytic colitis, diversion colitis, Behcet's disease, or indeterminate colitis.

Item 6. The method of any one of items 1-5, wherein *R. gnavus* has at least 5% relative abundance in the subject.

Item 7. The method of item 6, wherein *R. gnavus* has at least 10%, 20%, 30%, or 40% relative abundance in the subject.

Item 8. The method of any one of items 1-7, wherein the strain of *R. gnavus* is *R. gnavus* group IBD.

Item 9. The method of any one of items 1-8, wherein the *R. gnavus* comprises adherence-related genes.

Item 10. The method of any one of items 1-9, wherein the *R. gnavus* comprises genes involved in glycine-betaine transport.

Item 11. The method of any one of items 1-10, wherein the *R. gnavus* comprises at least one gene from Table 7.

Item 12. The method of items 1-11, wherein the *R. gnavus* comprises at least one cluster 1 gene from Table 7.

Item 13. The method of any one of items 1-12, wherein the *R. gnavus* comprises at least one cluster 2 gene from Table 7.

Item 14. The method of any one of items 1-13, wherein the *R. gnavus* comprises at least one cluster 3 gene from Table 7.

Item 15. The method of any one of items 1-14, wherein the *R. gnavus* comprises at least one cluster 4 gene from Table 7.

Item 16. The method of item 11, wherein the *R. gnavus* comprises all the genes from Table 7.

Item 17. The method of any one of items 1-16, wherein the *R. gnavus* is missing the Acetyl-CoA synthetase gene.

Item 18. The method of any one of items 1-17, wherein the *R. gnavus* is missing the corrinoid iron-sulfur small subunit.

Item 19. The method of any one of items 1-18, wherein the *R. gnavus* comprises genes for mucus utilization.

Item 20. The method of any one of items 1-19, wherein the *R. gnavus* comprises at least one glycoside hydrolase gene.

Item 21. The method of item 20, wherein the *R. gnavus* comprises at least one of the glycoside hydrolase genes identified in Table 9.

Item 22. The method item 21, wherein the *R. gnavus* comprises at least one of the glycoside hydrolase genes chosen from: g000676, g001578, g001597, g002881, g002982, g003046, g003139, g003144, g003577, g003631, g004607, g005357, g006085, g006118, and g007627.

Item 23. The method of item 20, wherein the *R. gnavus* comprises at least 2, 3, 4, 5, 6, 7, 8, 9, 10, 11, 12, 13, 14, or 15 of the glycoside hydrolase genes chosen from: g000676, g001578, g001597, g002881, g002982, g003046, g003139, g003144, g003577, g003631, g004607, g005357, g006085, g006118, and g007627.

Item 24. The method of any one of item 1-23, wherein multiple samples of the subject's gut microbiome are obtained over time.

Item 25. The method of item 24, wherein the relative abundance of *R. gnavus* varies over time.

Item 26. The method of item 25, wherein the relative abundance differs between samples by at least 5%, 10%, 15%, 20%, 25%, or 30%.

Item 27. The method of any one of item 1-26, wherein the gut microbiome sample is obtained from stool.

Item 28. The method of any one of items 1-27, wherein the gut microbiome sample is obtained from a biopsy of the mucus lining of the gastrointestinal tract.

Item 29. The method of item 28, wherein the mucus lining of the gastrointestinal tract is the mucus lining of the small intestine.

Item 30. The method of item 28, wherein the mucus lining of the gastrointestinal tract is the mucus lining of the large intestine.

Item 31. The method of any one of items 2 or 4-30, wherein the IBD therapy comprises
  a. at least one pharmaceutical composition;
  b. at least one phage therapy;
  c. at least one probiotic agent;
  d. at least one lifestyle modification;
  e. at least one alternative medicine; and/or
  f. surgery.

Item 32. The method of item 31, wherein the IBD therapy comprises at least one pharmaceutical composition.

Item 33. The method of any one of items 31-32, wherein the IBD therapy comprises at least one phage therapy.

Item 34. The method of any one of items 31-33, wherein the IBD therapy comprises at least one probiotic agent.

Item 35. The method of any one of items 31-34, wherein the IBD therapy comprises at least one lifestyle modification.

Item 36. The method of any one of items 31-35, wherein the IBD therapy comprises at least one alternative medicine.

Item 37. The method of any one of items 31-36, wherein the IBD therapy comprises at least one surgery.

Item 38. The method of any one of items 31-37, wherein at least one pharmaceutical composition is chosen from at least one antimicrobial agent, aminosalicylate, corticosteroid, immune system suppressor, anti-diarrheal agent, and pain reliever.

Item 39. The method of any one of items 1-2 or 4-38, wherein the antimicrobial agent is chosen from benzylpenicillin, piperacillin-tazobactam, meropenem, clindamycin, metronidazole, moxifloacin, vancomycin, tigecycline, bacitracin, and ciprofloxacin.

Item 40. The method of any one of items 38-39, wherein the aminosalicylates are chosen from 5-aminosalicylates, sulfasalazine, mesalamine, balsalazide, and olsalazine.

Item 41. The method of any one of items 38-40, wherein the at least one corticosteroid is chosen from prednisone and hydrocortisone.

Item 42. The method of any one of items 38-41, wherein the at least one immune system suppressor is chosen from at least one azathioprine, mercaptopurine, cyclosporine, TNF-alpha inhibitors, methotrexate, integrin inhibitors, and ustekinumab.

Item 43. The method of item 42, wherein the at least one TNF-alpha inhibitor is chosen from an anti-TNF-alpha antibody or antigen binding fragment thereof.

Item 44. The method of item 43, wherein the anti-TNF-alpha antibody or antigen binding fragment thereof is chosen from infliximab, adalimumab, golimumab, and antigen binding fragments thereof.

Item 45. The method of any one of items 42-44, wherein the at least one integrin inhibitor is chosen from an anti-integrin antibody or antigen binding fragment thereof.

Item 46. The method of item 45, wherein the anti-integrin antibody or antigen binding fragment thereof is chosen from natalizumab, vedolizumab, and antigen binding fragments thereof.

Item 47. The method of any one of items 38-46, wherein the anti-diarrheal agent is chosen from a fiber supplement (such as *psyllium* powder or methylcellulose) or loperamide.

Item 48. The method of any one of items 38-47, wherein the pain reliever is acetaminophen.

Item 49. The method of any one of items 38-48, wherein the pain reliever is not ibuprofen, naproxen sodium, or diclofenac sodium.

Item 50. The method of any one of items 31-49, wherein the at least one probiotic agent comprises one or more normal inhabitants of the human intestinal tract.

Item 51. The method of item 50, wherein the at least one probiotic agent is chosen from *Bacteroides, Prevotella, Porphyromonas, Fusobacterium, Sutterella, Bilophila, Campylobacter, Wolinella, Butyrovibrio, Megamonas, Desulfomonas, Desulfovibrio, Bifidobacterium, Lactobacillus, Eubacterium, Actinomyces, Eggerthella, Coriobacterium, Propionibacterium, Bacillus, Peptostreptococcus, Peptococcus, Acidaminococcus, Ruminococcus, Megasphaera, Gaffkya, Coprocaccus, Veillonella, Sarcina, Clostridium, Aerococcus, Streptococcus, Enterococcus, Pediococcus, Micrococcus, Staphylococcus, Corynebacterium*, Enterobacteriaceae, Pseudomonadaceae, and mixtures thereof.

Item 52. The method of any one of items 31-51, wherein at least one lifestyle modification is chosen from stopping smoking, stopping isotretinoin use, stopping nonsteroidal anti-inflammatory medication use, and dietary modification, and at least one alternative medicine.

Item 53. The method of item 52, wherein dietary modification is chosen from iron supplements, B-12 supplements or shots, calcium supplements, vitamin D supplements, enteral nutrition, parenteral nutrition, a low-residue and/or low fiber diet, reducing dairy products, reducing lactose consumption, a low-fat diet, avoiding uncooked fruits and vegetables, reducing irritating foods (including reducing foods in the cabbage family (broccoli, cauliflower, cabbage), reducing nuts and seed, reducing corn and popcorn, reducing spicy foods, reducing alcohol, and reducing caffeine), eating smaller and more frequent meals, drinking more liquids, and taking a multivitamin.

Item 54. The method of any one of items 31-53, wherein at least one lifestyle modification is chosen from exercise, biofeedback, and regular relaxation and breathing exercises.

Item 55. The method of any one of items 31-54, wherein the at least one alternative medicine comprises fish oil supplement, aloe vera supplement, turmeric or curcumin supplement, and acupuncture.

Item 56. The method of any one of items 31-55, wherein the surgery is chosen from removing a bowel obstruction, repairing or removing ulcers, draining and/or repairing abscesses, repairing or removing fistulas, removing inflamed and/or narrowed portions of the gastrointestinal tract, proctocolectomy, and strictureplasty.

Item 57. The method of any one of items 31-56, wherein the phage therapy is lytic phage specific for *R. gnavus*.

Item 58. The method of any one of items 31-57, wherein the lytic phage is obtained from stool samples.

Item 59. The method of any one of items 1-56, wherein further diagnostic information is obtained from a procedure chosen from at least one of colonoscopy, flexible sigmoidoscopy, upper endoscopy, capsule endoscopy, double-balloon endoscopy, x-ray, CT scan, MRI, and small bowel imaging.

Item 60. A kit to detect *R. gnavus* from a gut microbiome sample comprising
  a. an agent for detecting *R. gnavus* and/or *R. gnavus* group IBD;
  b. optionally buffers and/or reaction solutions.

Item 61. The kit of item 58, wherein the kit can detect *R. gnavus* group IBD.

Item 62. The kit of any one of items 58-59, wherein the agent for detecting *R. gnavus* and/or *R. gnavus* group IBD is chosen from:
  a. at least one nucleic acid probe capable of hybridizing to a *R. gnavus* nucleic acid;
  b. at least one primer pair for amplifying a *R. gnavus* nucleic acid;
  c. an antibody or antigen binding fragment thereof specific for *R. gnavus*.

Item 63. The kit of any one of items 58-60, wherein the *R. gnavus* nucleic acid is at least one of the genes in Table 7 or Table 9.

Item 64. The kit of any one of items 58-61, wherein the *R. gnavus* nucleic acid is a 16S rRNA gene.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method of treating IBD in a human subject comprising
  a. determining from a gut microbiome sample whether the gut microbiome comprises *Ruminococcus gnavus*,
  b. determining relative abundance of *R. gnavus*, and if the relative abundance of *R. gnavus* is at least 5%,
  c. diagnosing the subject as having IBD, and
  d. administering to the subject an effective amount of at least one antimicrobial agent effective for eliminating or suppressing *R. gnavus*.

2. A method of treating IBD in a human subject comprising
  a. determining from a gut microbiome sample whether the gut microbiome comprises *R. gnavus*;
  b. determining relative abundance of *R. gnavus*; and
  if the relative abundance of *R. gnavus* is at least 5%,
  c. diagnosing the subject as having IBD, and
  d. administering an effective amount of at least one IBD therapy to the subject having a gut microbiome comprising *R. gnavus*.

3. A method of diagnosing IBD in a human subject comprising:

a. determining from a gut microbiome sample whether the gut microbiome comprises *R. gnavus*;
b. determining relative abundance of *R. gnavus*; and if the relative abundance of *R. gnavus* is at least 5%,
c. diagnosing the subject as having IBD.

4. The method of claim 1, wherein the IBD is Crohn's disease, ulcerative colitis, collagenous colitis, lymphocytic colitis, diversion colitis, Behcet's disease, or indeterminate colitis.

5. The method of claim 1, wherein *R. gnavus* has at least 10%, 20%, 30% or 40% relative abundance in the subject.

6. The method of claim 1, wherein the strain of *R. gnavus* is *R. gnavus* group IBD and optionally wherein the *R. gnavus* comprises:
  a. adherence related genes;
  b. genes involved in glycine betaine transport;
  c. at least one gene from any one of clusters 1, 2, 3, and 4;
  d. at least one cluster 1 gene;
  e. at least one cluster 2 gene;
  f. at least one cluster 3 gene;
  g. at least one cluster 4 gene; or
  h. all genes of clusters 1, 2, 3, and 4;
  wherein for any of parts (a)-(h)
    i. the cluster 1 gene is chosen from G007090, g007091, g007092, g007093, G007094, and G007095 (10);
    ii. the cluster 2 gene is chosen from g006853 and g006854;
    iii. the cluster 3 gene is chosen from g001652, g001653, g001654, g001655, g001656, g001657, and g001658; and g005308, g005309,
    iv. the cluster 4 gene is chosen from g005306, g005307, g005310, g005311, g005312, and g005313.

7. The method of claim 1, wherein the *R. gnavus* is missing the Acetyl-CoA synthetase gene.

8. The method of claim 1, wherein the *R. gnavus* is missing the corrinoid iron-sulfur small subunit.

9. The method of claim 1, wherein the *R. gnavus* comprises genes for mucus utilization.

10. The method of claim 1, wherein the *R. gnavus* comprises at least one glycoside hydrolase gene.

11. The method of claim 10, wherein the *R. gnavus* comprises at least one of the glycoside hydrolase genes chosen from g000635, g000676, g001562, g001578, g001597, g002881, g002982, g003046, g003139, g003144, g003577, g003631, g004607, g005357, g006085, g006118, and g007627.

12. The method of claim 10, wherein the *R. gnavus* comprises at least one of the glycoside hydrolase genes chosen from: g000676, g001578, g001597, g002881, g002982, g003046, g003139, g003144, g003577, g003631, g004607, g005357, g006085, g006118, and g007627.

13. The method of claim 10, wherein the *R. gnavus* comprises at least 2, 3, 4, 5, 6, 7, 8, 9, 10, 11, 12, 13, 14, or 15 of the glycoside hydrolase genes chosen from: g000676, g001578, g001597, g002881, g002982, g003046, g003139, g003144, g003577, g003631, g004607, g005357, g006085, g006118, and g007627.

14. The method of claim 3, wherein multiple samples of the subject's gut microbiome are obtained over time and the relative abundance of *R. gnavus* is determined.

15. The method of claim 5, wherein the relative abundance of *R. gnavus* varies over time.

16. The method of claim 15, wherein the relative abundance differs between samples by at least 5%, 10%, 15%, 20%, 25%, or 30%.

17. The method of claim 3, wherein the gut microbiome sample is obtained from stool.

18. The method of claim 3, wherein the gut microbiome sample is obtained from a biopsy of the mucus lining of the gastrointestinal tract.

19. The method of claim 18, wherein the mucus lining of the gastrointestinal tract is the mucus lining of the small intestine.

20. The method of claim 18, wherein the mucus lining of the gastrointestinal tract is the mucus lining of the large intestine.

21. The method of claim 3, wherein multiple samples of the subject's gut microbiome are obtained over time and the relative abundance of *R. gnavus* is determined.

* * * * *

UNITED STATES PATENT AND TRADEMARK OFFICE
CERTIFICATE OF CORRECTION

PATENT NO. : 11,806,372 B2
APPLICATION NO. : 16/604866
DATED : November 7, 2023
INVENTOR(S) : Andrew Brantley Hall et al.

Page 1 of 2

It is certified that error appears in the above-identified patent and that said Letters Patent is hereby corrected as shown below:

In the Claims

Column 36
Line 49, Claim 1, delete "," insert --;--
Line 50, Claim 1, delete "," insert --;--

Column 37
Line 8, Claim 4, delete "Behcet's", insert --Behçet's--
Line 27, Claim 6, "g006853", should be "*g006853*"
Line 28, Claim 6, "g006854", should be "*g006854*"
Line 29, Claim 6, "g001652", should be "*g001652*"
Line 30, Claim 6, "g001653" "g001654" "g001655" "g001656" "g001657", should be "*g001653*" "*g001654*" "*g001655*" "*g001656*" "*g001657*"
Line 31, Claim 6, "g001658", should be "*g001658*"
Line 31, Claim 6, delete "g005308, g005309,"
Line 32, Claim 6, "g005306" "g005307", should be "*g005306*" "*g005307*"
Line 32, Claim 6, after "g005307,", insert --*g005308, g005309*,--
Line 33, Claim 6, "g005310" "g005311" "g005312" and "g005313", should be "*g005310*" "*g005311*" "*g005312*" and "*g005313*"

Column 38
Line 3, Claim 11, "g000635" "g000676" "g001562" "g001578", should be "*g000635*" "*g000676*" "*g001562*" "*g001578*"
Line 4, Claim 11, "g001597" "g002881" "g002982" "g003046" "g003139" "g003144", should be "*g001597*" "*g002881*" "*g002982*" "*g003046*" "*g003139*" "*g003144*"
Line 5, Claim 11, "g003577" "g003631" "g004607" "g005357" "g006085" "g006118", should be "*g003577*" "*g003631*" "*g004607*" "*g005357*" "*g006085*" "*g006118*"
Line 6, Claim 11, "g007627", should be "*g007627*"
Line 9, Claim 12, "g000676" "g001578" "g001597" "g002881", should be "*g000676*" "*g001578*" "*g001597*" "*g002881*"

Signed and Sealed this
Thirtieth Day of January, 2024

Katherine Kelly Vidal
*Director of the United States Patent and Trademark Office*

CERTIFICATE OF CORRECTION (continued)
U.S. Pat. No. 11,806,372 B2

Line 10, Claim 12, "g002982" "g003046" "g003139" "g003144" "g003577" "g003631", should be "*g002982*" "*g003046*" "*g003139*" "*g003144*" "*g003577*" "*g003631*"
Line 11, Claim 12, "g004607" "g005357" "g006085" "g006118" and "g007627", should be "*g004607*" "*g005357*" "*g006085*" "*g006118*" and "*g007627*"
Line 14, Claim 13, "g000676", should be "*g000676*"
Line 15, Claim 13, "g001578" "g001597" "g002881" "g002982" "g003046" "g003139", should be "*g001578*" "*g001597*" "*g002881*" "*g002982*" "*g003046*" "*g003139*"
Line 16, Claim 13, "g003144" "g003577" "g003631" "g004607" "g005357" "g006085", should be "*g003144*" "*g003577*" "*g003631*" "*g004607*" "*g005357*" "*g006085*"
Line 17, Claim 13, "g006118" and "g007627", should be "*g006118*" and "*g007627*"